(12) United States Patent
Stahl et al.

(10) Patent No.: US 9,957,217 B2
(45) Date of Patent: May 1, 2018

(54) CONVERSION OF ALCOHOLS TO CARBOXYLIC ACIDS USING HETEROGENEOUS PALLADIUM-BASED CATALYSTS

(71) Applicant: Wisconsin Alumni Research Foundation, Madison, WI (US)

(72) Inventors: Shannon S. Stahl, Madison, WI (US); Adam B. Powell, Wexford, PA (US); Thatcher W. Root, Madison, WI (US); David S. Mannel, Madison, WI (US); Maaz S. Ahmed, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days. days.

(21) Appl. No.: 15/420,378

(22) Filed: Jan. 31, 2017

(65) Prior Publication Data

US 2017/0137362 A1 May 18, 2017

Related U.S. Application Data

(62) Division of application No. 14/702,266, filed on May 1, 2015, now Pat. No. 9,593,064.

(60) Provisional application No. 61/987,080, filed on May 1, 2014.

(51) Int. Cl.
*C07C 51/235* (2006.01)
*B01J 21/18* (2006.01)
*B01J 27/057* (2006.01)
*B01J 35/00* (2006.01)
*C07D 307/68* (2006.01)

(52) U.S. Cl.
CPC ............ *C07C 51/235* (2013.01); *B01J 21/18* (2013.01); *B01J 27/0576* (2013.01); *B01J 35/0006* (2013.01); *C07D 307/68* (2013.01); *C07C 2101/14* (2013.01)

(58) Field of Classification Search
CPC .................................................... C07C 51/235
See application file for complete search history.

(56) References Cited

PUBLICATIONS

Bai, X-F, et al., "Hydrosilane and bismuth-accelerated palladium catalyzed aerobic oxidative esterification of benzylic alcohols with air," Chem. Commun. (2012), vol. 48, pp. 8592-8594.

*Primary Examiner* — Noble E Jarrell
*Assistant Examiner* — John S Kenyon
(74) *Attorney, Agent, or Firm* — Boyle Fredrickson S.C.

(57) ABSTRACT

Disclosed are methods for synthesizing an ester or a carboxylic acid from an organic alcohol. To form the ester one reacts, in the presence of oxygen gas, the alcohol with methanol or ethanol. This reaction occurs in the presence of a catalyst comprising palladium and a co-catalyst comprising bismuth, tellurium, lead, cerium, titanium, zinc and/or niobium (most preferably at least bismuth and tellurium). Alternatively that catalyst can be used to generate an acid from that alcohol, when water is also added to the reaction mix.

6 Claims, 22 Drawing Sheets

FIG. 5

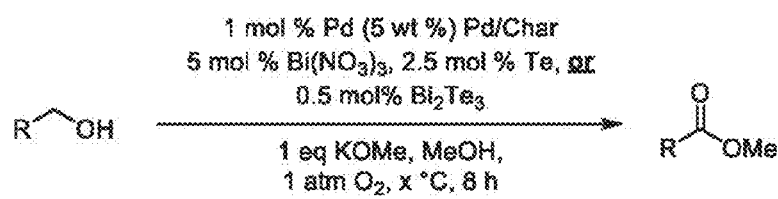

| Entry | Substrate | Additives | Yield (Conv)[a] | | |
|---|---|---|---|---|---|
| | | | 25 °C | 50 °C | 60 °C |
| 1 | 4-methylbenzyl alcohol | Bi(NO$_3$)$_3$, Te / Bi$_2$Te$_3$ | 85 (100) / 85 (100) | 83 (100) / 83 (100) | 95 (100) / 85 (100) |
| 2 | 4-methoxybenzyl alcohol | Bi(NO$_3$)$_3$, Te / Bi$_2$Te$_3$ | 100 (100) / 90 (90) | 95 (100) / 95 (100) | 100 (100) / 100 (100) |
| 3 | 4-(trifluoromethyl)benzyl alcohol | Bi(NO$_3$)$_3$, Te / Bi$_2$Te$_3$ | 80 (80) / 52 (100)[b] | 89 (100) / 47 (100)[b] | 90 (100) / 85 (95) |
| 4 | alkyl alcohol | Bi(NO$_3$)$_3$, Te / Bi$_2$Te$_3$ | 60 (64) / 52 (54) | 88 (90) / 79 (89) | 89 (93) / 75 (80) |
| 5 | cyclohexylmethanol | Bi(NO$_3$)$_3$, Te / Bi$_2$Te$_3$ | 46 (48) / 13 (15) | 75 (92) / 86 (87) | 75 (100) / 70 (88) |
| 6 | 3-(benzyloxy)propan-1-ol | Bi(NO$_3$)$_3$, Te / Bi$_2$Te$_3$ | 31 (41) / 18 (24) | 65 (67) / 50 (70) | 72 (100)[c] / 30 (48)[c] |
| 7 | 3-phenylpropan-1-ol | Bi(NO$_3$)$_3$, Te / Bi$_2$Te$_3$ | 54 (54) / 40 (41) | 69 (70) / 80 (80) | 92 (92) / 66 (68) |
| 8 | thiophen-2-ylmethanol | Bi(NO$_3$)$_3$, Te / Bi$_2$Te$_3$ | 98 (98) / 80 (100) | 89 (90) / 72 (94) | 85 (90) / 85 (90) |

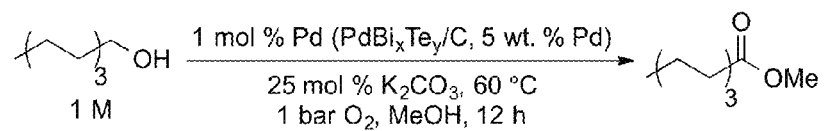
FIG. 12A
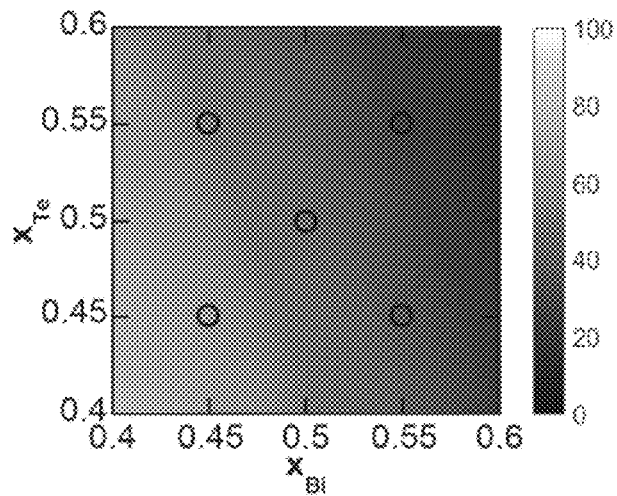
FIG. 12B
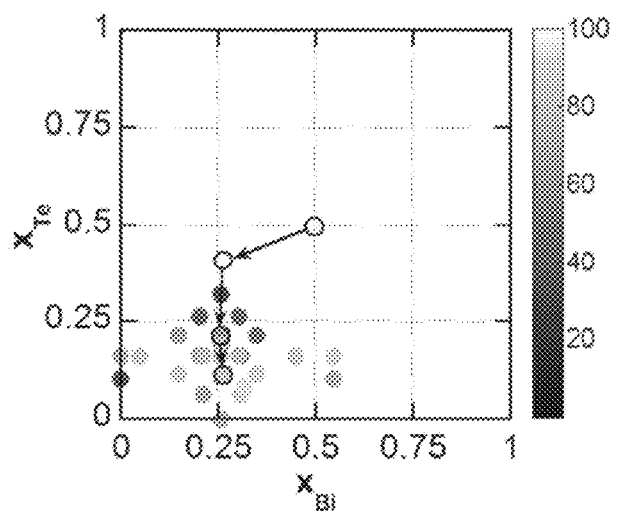

FIG. 13
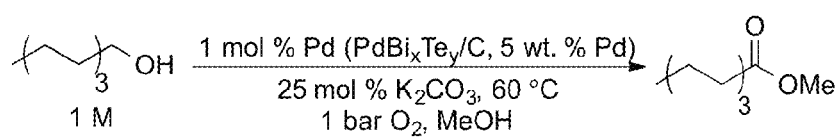
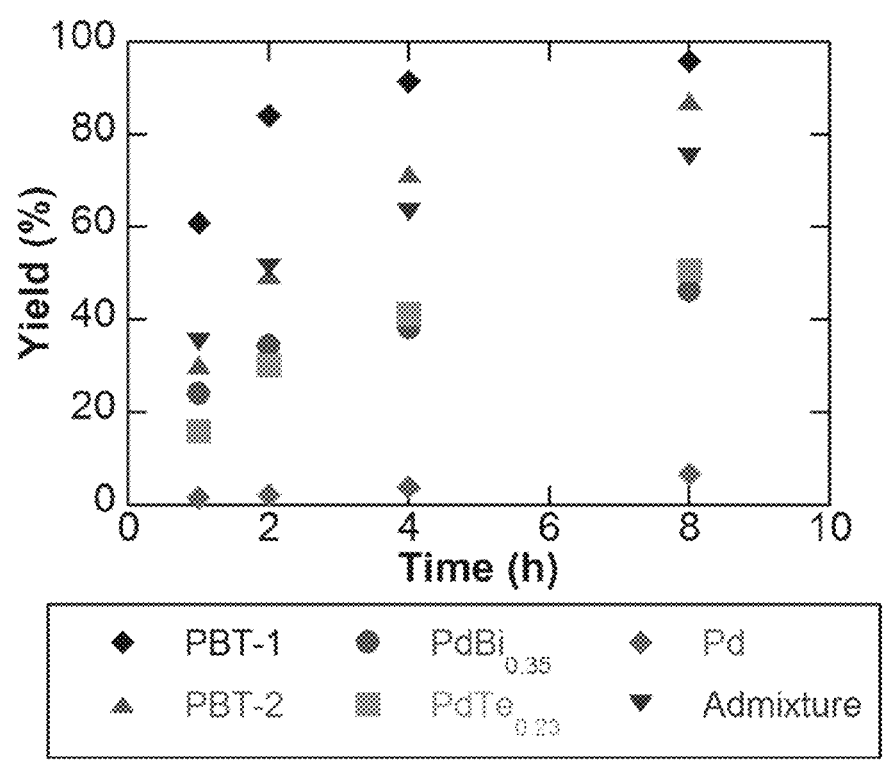

FIG. 18A
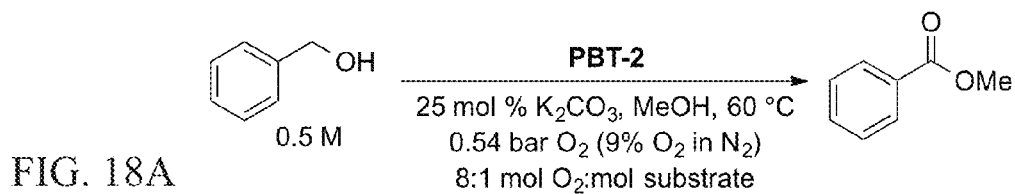
FIG. 18B
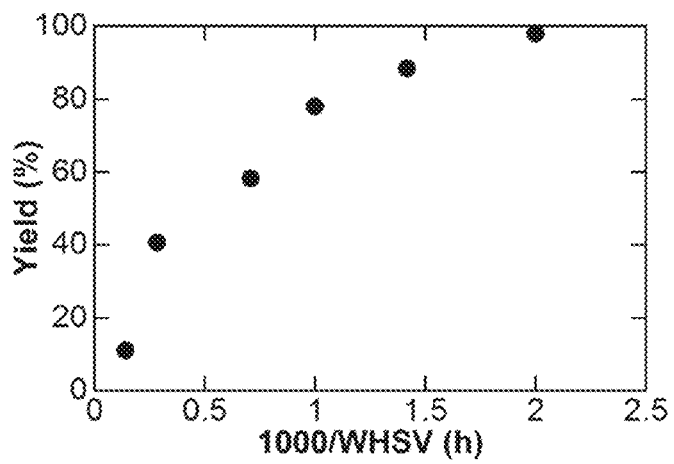
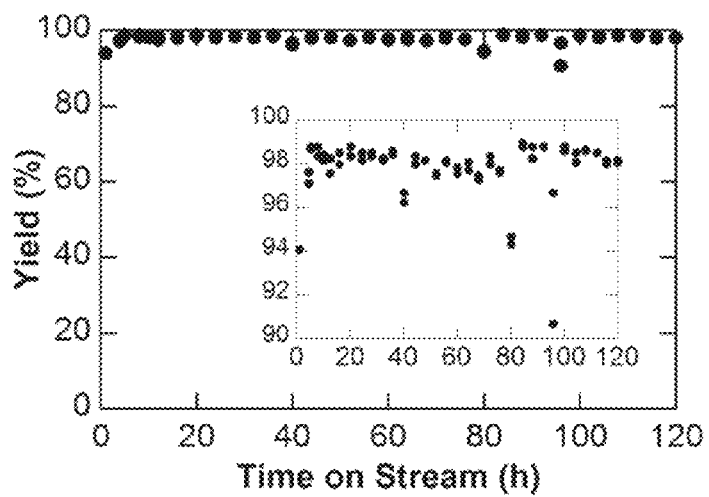

FIG. 20
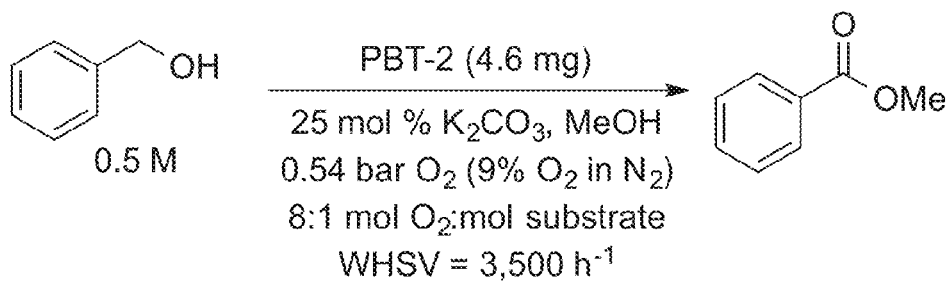
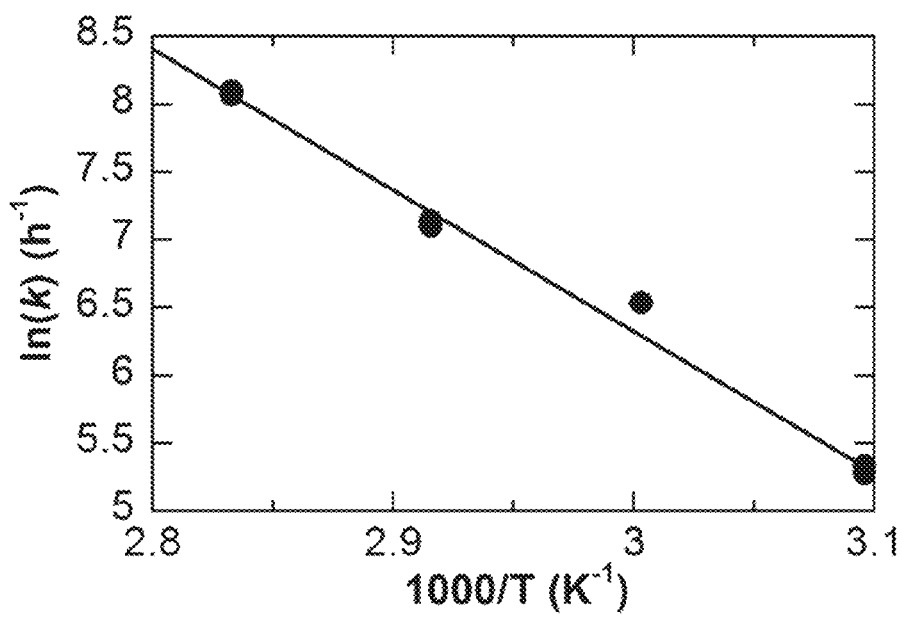

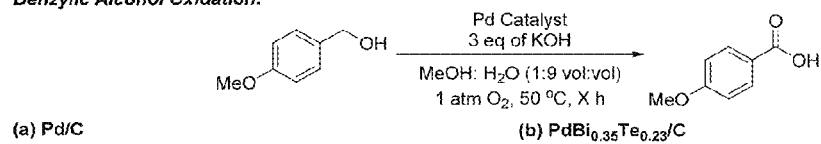
(a) Pd/C  (b) PdBi$_{0.35}$Te$_{0.23}$/C
FIG. 21A
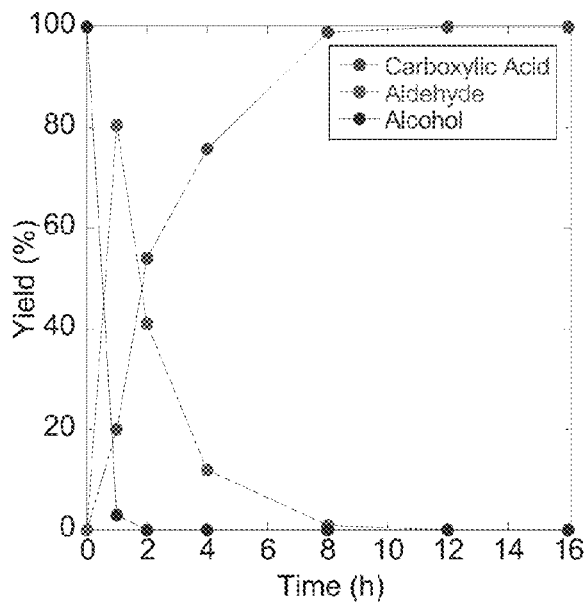
FIG. 21B
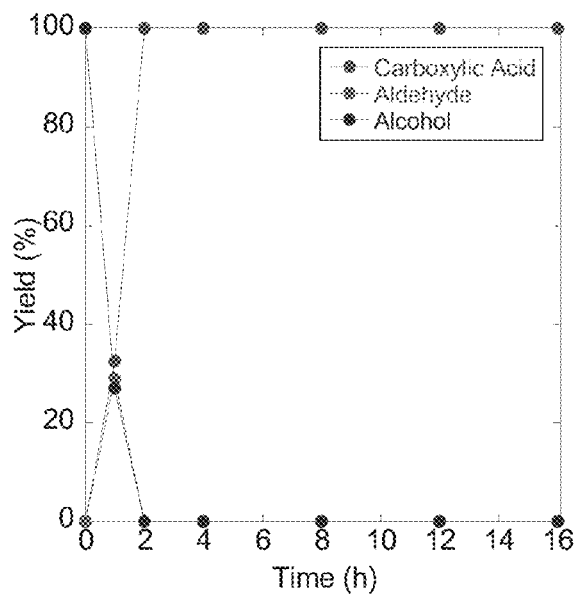

*Aliphatic Alcohol Oxidation:*
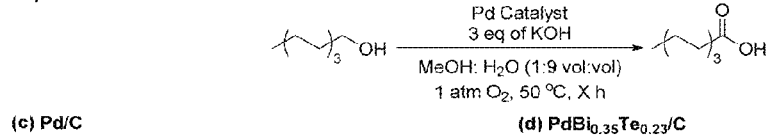
(c) Pd/C          (d) PdBi$_{0.35}$Te$_{0.23}$/C
FIG. 21C
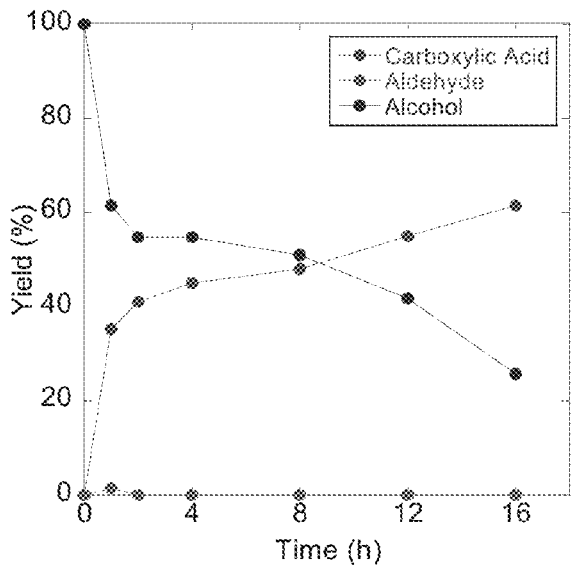
FIG. 21D
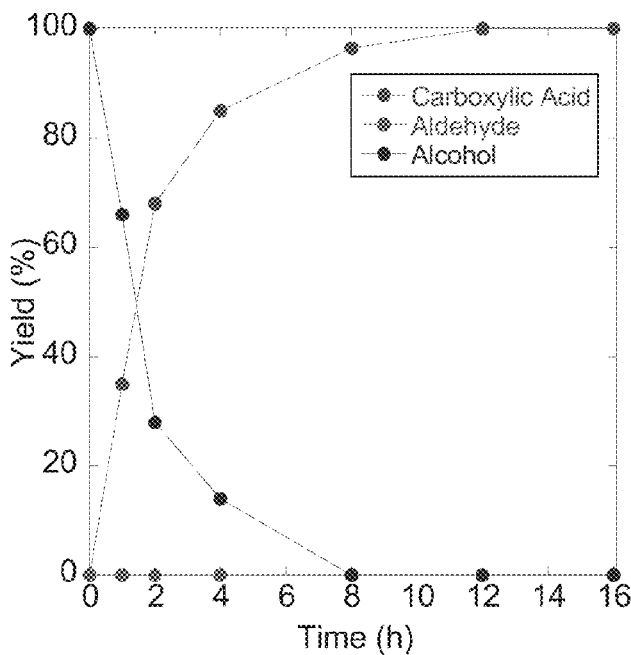

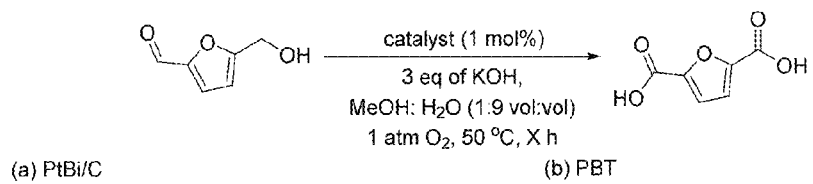
(a) PtBi/C  (b) PBT
FIG. 24A
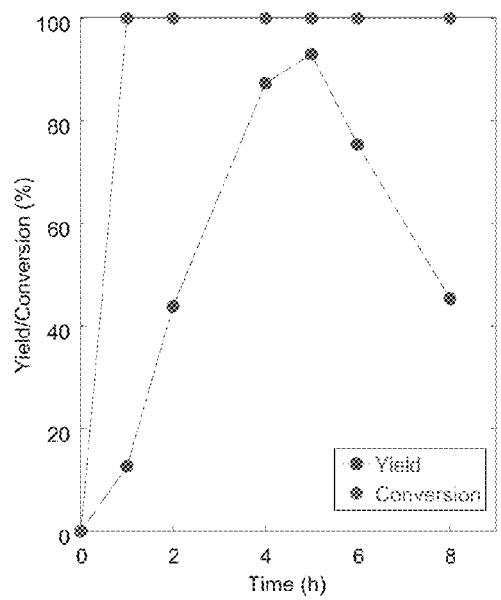
FIG. 24B
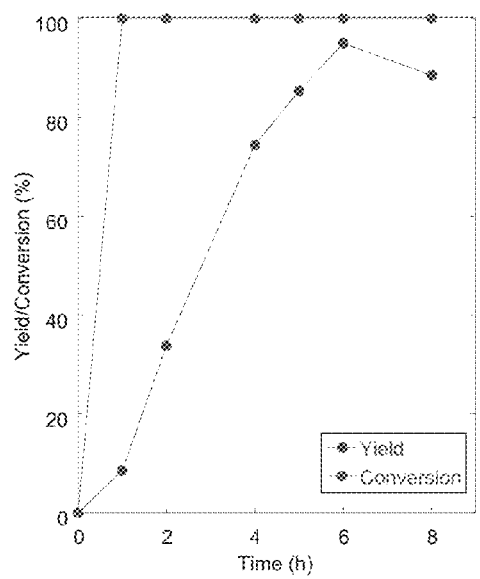

CONVERSION OF ALCOHOLS TO CARBOXYLIC ACIDS USING HETEROGENEOUS PALLADIUM-BASED CATALYSTS

CROSS-REFERENCE TO RELATED APPLICATIONS

This application is a divisional of U.S. patent application Ser. No. 14/702,266, filed May 1, 2015, which claims priority to U.S. Provisional Patent Application No. 61/987,080 filed on May 1, 2014. Both of these applications are incorporated by reference herein in their entireties.

STATEMENT REGARDING FEDERALLY SPONSORED RESEARCH/DEVELOPMENT

Not applicable.

BACKGROUND OF THE INVENTION

The present invention relates to improved methods for synthesizing esters and carboxylic acids from organic alcohols. In particular, it relates to performing such synthesis reactions in the presence of palladium-based catalysts that also include a co-catalyst comprising bismuth, tellurium, lead, cerium, titanium, zinc and/or niobium (most preferably bismuth and tellurium).

Heterogeneous Pd catalysts have been used in organic chemistry for the reduction of some organic compounds. Prominent examples include simple supported catalysts such as Pd/C and Pd/Al$_2$O$_3$, as well as more complex variants such as Lindlar's catalyst, in which Pd/CaCO$_3$ is modified by Pb(OAc)$_2$ and quinoline. Similar catalysts for selective oxidation of organic molecules have been developed, but effective examples are rare.

Adam's catalyst (PtO$_2$) is typically used as a hydrogenation catalyst, but it also mediates aerobic oxidation of primary alcohols to carboxylic acids. High catalyst loading is often required in the latter application (e.g., 0.6 equiv Pt$^{3b}$), and other reagents, such as the Jones reagent (CrO$_3$/H$_2$SO$_4$) or bleach/TEMPO, tend to be more reliable. Homogeneous and heterogeneous Pd catalysts have been studied for aerobic alcohol oxidation, but this work has mostly focused on conversion of alcohols to aldehydes and ketones. In any event, methods for oxidation of primary alcohols to carboxylic acids and esters are limited with respect to substrate scope (e.g. typically mostly effective with benzylic alcohols) and/or catalyst accessibility.

The literature also refers to homogeneous and heterogeneous Pd based catalysts for the oxidation of alcohols to aldehydes and ketones within the domain of sugar chemistry. Further oxidation of aldehydes to the corresponding carboxylic acid has proved to be challenging with respect to both substrates accessible, or the preparation of the catalyst.

This is particularly of interest as transformation of hydrocarbon feedstocks into value added fine chemicals or pharmaceuticals requires the introduction of various functional groups in the form of a more oxidized molecule. Some reaction conditions/materials have safety drawbacks such as the use of toxic, corrosive, flammable, and/or explosive chemicals, and/or also have low atom efficiency because of stoichiometric byproducts.

The use of O$_2$ for oxidation provides a nontoxic and noncorrosive oxidant alternative with high atom efficiency and water as a benign byproduct. Oxidation of alcohols to aldehydes and ketones has been well studied in the literature, while aerobic oxidation of alcohols to other products such as methyl esters has fewer catalytic studies.

Heterogeneous catalysts have many advantages over homogeneous catalysts including ease of separation and longevity. However, heterogeneous catalysts can be lacking in selectivity, especially towards diverse functional groups present in fine chemicals and pharmaceuticals. Few examples exist of heterogeneous catalysts being able to tolerate wide ranges of functional groups with acceptable selectivity. Most of these examples have limitations such as tedious/costly catalyst syntheses or require specialized equipment for the synthesis.

Another concern is catalysts that suffer from a lack of recyclability and/or longevity.

In H. Kimura et al., Palladium Based Multi-Component Catalytic Systems For The Alcohol To Carboxylate Oxidation Reaction, 95 J. Applied Catalysis A: General 143-169 (1993) there was discussion of multi-component palladium bismuth catalysts (with a variety of different possible additional additives) used to convert certain alcohols to acids. The article did not relate to esterification reactions, and suggested a variety of undesirable limitations even in the context of acids.

Hence, there remains a need for improved methods of forming methyl esters and carboxylic acids, particularly when using primary alcohols as a starting material.

SUMMARY OF THE INVENTION

Below we describe palladium-based catalysts that promote efficient aerobic oxidation of primary alcohols to esters and acids, including benzylic, cyclic and aliphatic examples. We have particularly discovered that use of certain co-catalysts with the palladium significantly improves the efficiency and selectivity of these reactions, and thereby enables broader substrate scope and functional-group compatibility.

In one aspect the invention provides a method for synthesizing an ester from two alcohols. One reacts, in the presence of oxygen gas, an alkyl alcohol with less than three carbons with a compound of the formula R$^1$CH$_2$OH. The reaction is also in the presence of a catalyst comprising palladium and at least one co-catalyst comprising bismuth and/or tellurium.

Preferred conditions include an absence of water (to minimize side reactions). Note that allowing the reaction to proceed for excess time increases side products as well in some syntheses.

Various supports for the catalysts have proven suitable. In this regard, we have successfully used activated carbon, activated charcoal, and metal oxides such as Al$_2$O$_3$ for this purpose. A large excess of MeOH or ethanol without water leads to the ester, whereas a large excess of water directs the reaction to the acid. We prefer to use minor amounts of methanol in even acid examples to solubilize the organic alcohols.

An ester of the following formula can be formed:

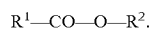

R$^1$—CO—O—R$^2$.

R$^1$ comprises an alkyl, cyclic, aryl, heterocyclic, arene, amine, ether, ester or protected alcohol moiety, with or without sulfur or halogen content. R$^2$ is an alkyl moiety having less than three carbons. For example methanol or ethanol can be reacted with octanol or a benzyl alcohol.

Most preferably the palladium is present in excess of the bismuth and tellurium, and on an elemental carbon, activated carbon, or metal oxide based support. In any event, we prefer to use at least 0.5 mol percent palladium, at least 0.5 mol percent bismuth, and at least 0.5 mol percent tellurium in the catalyst.

In one form the bismuth is present as a salt and the tellurium is present in a metal form, where the bismuth salt is $Bi(NO_3)_3 \cdot 5H_2O$. Alternatively, both the bismuth and tellurium can be in the metal form so as to create a trimetallic catalyst.

Efficient reactions take place at 40° C., most preferably at about 60° C.

In another form the invention there is provided a method for synthesizing an ester from two alcohols where one reacts in the presence of oxygen gas, an alkyl alcohol having less than three carbons with a compound of the formula $R_1CH_2OH$. The reacting is in the presence of a catalyst comprising palladium and a co-catalyst comprising at least two of the following: bismuth, tellurium, lead, cerium, titanium, zinc and niobium.

An ester of the following formula is formed:

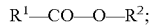

wherein $R^1$ comprises an alkyl, cyclic, aryl, heterocyclic, arene, amine, ether, ester or protected alcohol moiety, with or without sulfur or halogen content. $R^2$ is an alkyl moiety having less than three carbons.

In another aspect the invention provides a method for synthesizing an acid from an alcohol. One exposes a compound of the formula $R-CH_2-OH$ to oxygen gas and water so as to yield a compound of the formula RCOOH. The reaction is also in the presence of a catalyst comprising palladium and at least one co-catalyst comprising bismuth and/or tellurium. R comprises an alkyl, cyclic, aryl, heterocyclic, arene, amine, ether, ester or protected alcohol moiety, with or without sulfur or halogen content.

Preferred reaction conditions include the addition of a strong base, preferentially KOH, in the presence of water with 10% methanol added (to help increase the interaction between the substrate and the catalyst).

Again, most preferably the palladium is present in excess of the bismuth and tellurium, and on an elemental carbon based support. In any event, for this reaction we prefer at least 0.1 mol percent palladium, at least 0.01 mol percent bismuth, and at least 0.01 mol percent tellurium in the catalyst.

Again, in one form the bismuth is present in a salt form and the tellurium is present in a metal form, where the bismuth salt is $Bi(NO_3)_3 \cdot 5H_2O$. In another form the bismuth and tellurium are co-deposited onto the palladium catalyst forming a trimetallic catalyst.

Efficient reactions take place at above 40° C., most preferably at about 60° C.

In yet another form the invention provides a method for synthesizing an acid from an alcohol. One exposes a compound of the formula $R-CH_2-OH$ to oxygen gas and water so as to yield a compound of the formula RCOOH. The exposing is in the presence of a catalyst comprising palladium and also a co-catalyst comprising at least two of the following: bismuth, tellurium, lead, cerium, titanium, zinc and niobium. R is an alkyl, cyclic, aryl, heterocyclic, arene, amine, ether, ester or protected alcohol moiety, with or without sulfur or halogen content.

In sum, we have discovered that bismuth and tellurium (and to a lesser extent certain other additives), act in a synergistic manner with palladium to effect aerobic oxidation of alcohols to esters and acids (to the acid when substantial water is present). A wide range of starting substrate alcohols can be used, with high selectivity.

The above and still other advantages of the present invention will be apparent from the description that follows. It should be appreciated that the following description is merely of preferred embodiments of our invention. The claims should therefore be looked to in order to understand the full claimed scope of the invention.

BRIEF DESCRIPTION OF THE DRAWINGS

FIG. 5 depicts the impact of temperature variations on various esterification reactions.

FIG. 12A and FIG. 12B show response-surface-methodology data for PdBiTe catalyst optimization in the oxidative methyl esterification of 1-octanol, with a shading gradient reflecting the yield of methyl octanoate under the conditions indicated in the equation. FIG. 12A illustrates catalyst composition starting points for determination of the path of steepest ascent towards higher yields. FIG. 12B illustrates iterative path followed over three steps of catalyst optimization, starting at a 1:1:1 Pd:Bi:Te ratio (open circles), and catalyst activity data for PdBiTe compositions in the region of highest activity (shaded circles).

FIG. 13 shows reaction time-courses comparing the activity of the different catalysts for the oxidative methyl esterification of 1-octanol. PBT-1=$PdBi_{0.47}Te_{0.09}$; PBT-2= $PdBi_{0.35}Te_{0.23}$; Admixture=1 mol % Pd/charcoal (5 wt %), 5 mol % $Bi(NO_3)_3 \cdot 5H_2O$, 2.5 mol % Te.

FIGS. 18A and 18B show oxidative methyl esterification of benzyl alcohol under continuous-flow conditions with the PBT-2 catalyst. FIG. 18A shows assessment of different flow rates to identify the optimal WHSV. FIG. 18B shows long-term testing of the PBT-2 catalyst at a WHSV of 500 $h^{-1}$.

FIG. 19A shows loss of Pd, Bi and Te from the PBT-2 catalyst during continuous oxidative methyl esterification of benzyl alcohol (cf. FIG. 18B). FIG. 19B shows change in PBT-1 and PBT-2 catalyst compositions during long-term oxidation of benzyl alcohol, mapped onto the catalyst activity plot shown in FIG. 12B.

FIG. 20 is an Arrhenius plot of ln(k) vs 1000/T. Fitted parameters: $A=6\times10^{12}$ $s^{-1}$, $E_a=87\pm2.7$ kJ/mol.

FIGS. 21A-21D are time courses of the oxidation primary alcohol to the carboxylic acid. FIG. 21A is a time course using Pd/C to catalytically oxidize 4-methoxybenzyl alcohol; FIG. 21B is a time course using PBT to catalytically oxidize 4-methoxybenzyl alcohol; FIG. 21C is a time course using Pd/C to catalytically oxidize 1-octanol; FIG. 21D is a time course using PBT to catalytically oxidize 1-octanol. $^1$H NMR yields with trimethyl(phenyl)silane as internal standard (std. dev.±5%). Conditions: 1 mmol scale, [alcohol]=1 M, 1 mol % catalyst, 3 eq of KOH, methanol: water (1:9 vol:vol), 1 atm $O_2$, 50° C.

FIGS. 24A and 24B show time courses of the oxidation HMF to FDCA using industrial PtBi/C (FIG. 24A) and using PBT (FIG. 24B). HPLC yields with benzoic acid as internal standard. Conditions: 0.50 mmol scale, [alcohol]=1.8 M, 1 mol % catalyst, 3 eq of KOH, Methanol: Water (1:9 vol: vol), 1 atm 02, 50° C.

DETAILED DESCRIPTION

A variety of commercially available palladium sources were tested as potential catalysts at 1 mol % palladium loading for the oxidative esterification of octanol to methyl octanoate under 1 atm of $O_2$ in methanol. Both heterogeneous and homogeneous palladium sources were tested. See Table 1.

The relatively poor conversions and yields obtained with most initially tried catalysts, maximum yield 20% with 1% Pd/C and 5% Pd/Char (Char=charcoal), led us to experiment with additional co-catalysts. We then tried inclusion of 1 mol % $Bi(NO_3)_3.5H_2O$ in our reactions. This surprisingly resulted in significantly increased yields. For example, a yield of 60% was achieved with Pd/Char and $Bi(NO_3)_3.5H_2O$. See generally Table 1.

TABLE 1

Impact on yield of including bismuth in various catalyst systems

| | | Yield (Conv)$^a$ | |
|---|---|---|---|
| Entry | Catalyst | No $Bi(NO_3)_3$ | $Bi(NO_3)_3$$^b$ |
| 1 | 1 wt % Pd/C | 20 (22) | 45 (54) |
| 2 | 1 wt % Pd/$Al_2O_3$ | 6 (17) | 49 (65) |
| 3 | 2.5 wt % Pd/C | 7 (40) | 57 (58) |
| 4 | 5 wt % Pd/C | 10 (11) | 45 (61) |
| 5 | 5 wt % Pd/Char$^c$ | 16 (20) | 60 (60) |
| 6 | 30 wt % Pd/C | 5 (9) | 30 (39) |
| 7 | $PdCl_2$$^d$ | 0 (0) | 0 (0) |
| 8 | $Pd(OAc)_2$$^d$ | 0 (0) | 15 (17) |

$^a$Reactions performed on 1 mmol scale; [$RCH_2OH$] = 1M. $^1$H NMR yields with trimethoxybenzene as internal standard.
$^b$$Bi(NO_3)_3$ = $Bi(NO_3)_3$•$5H_2O$.
$^c$Char = charcoal.
$^d$20 mg activated carbon added.

The beneficial effect of $Bi(NO_3)_3.5H_2O$ prompted us to examine also including other additives in the reaction. Most, such as Cu, Ag and Sb sources, had a negligible or only slightly beneficial effect. However, tellurium exhibited a highly beneficial effect. For example, $Bi_2Te_3$, an alloy containing both Bi and Te, had a 87% yield of methyl octanoate.

Figure 1:
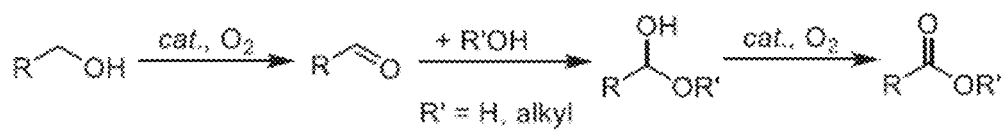
FIG. 1 depicts a generic representation of the methods of the present invention as applied to esterification.
Figure 2:
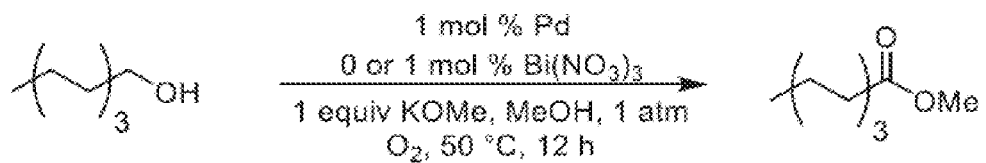
FIG. 2 depicts the esterification of octanol.
Figure 3:
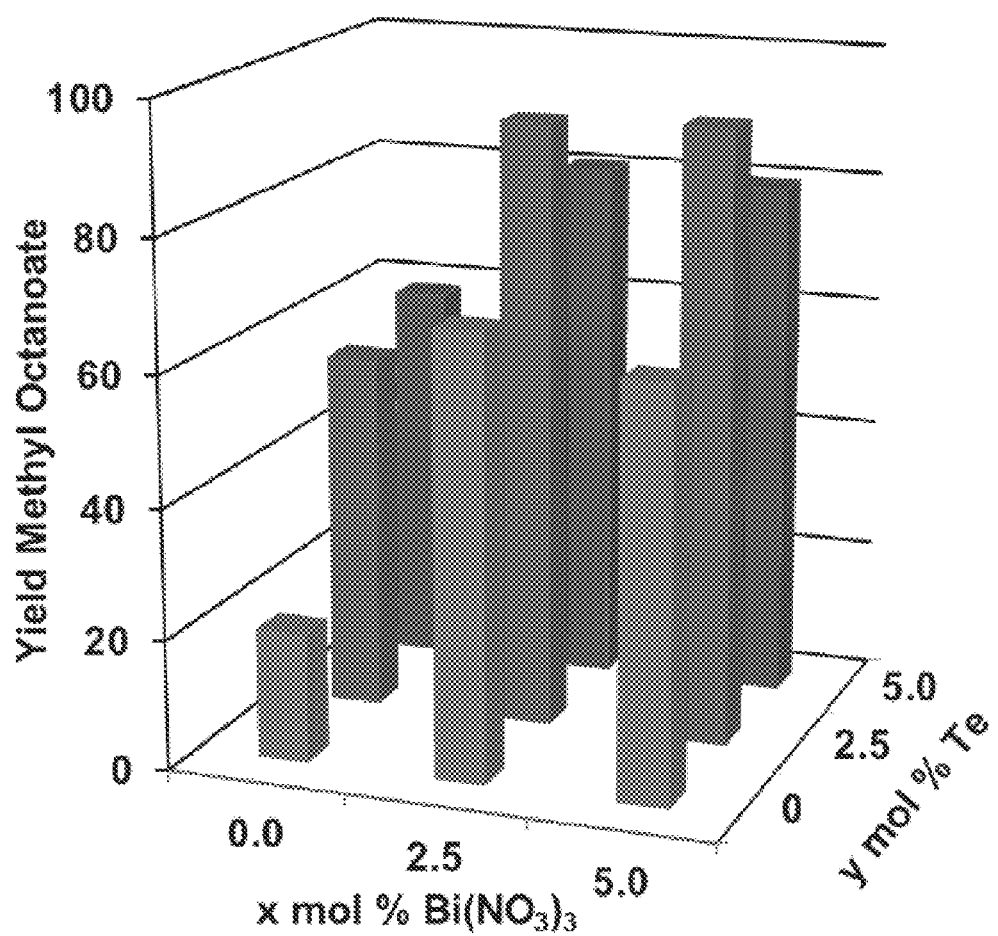
FIG. 3 depicts the impact of also adding varied amounts of tellurium to varied bismuth catalyst systems.

The synergistic effect of bismuth with the second additive was examined further, and highly desirable results were obtained with $Bi(NO_3)_3.5H_2O$/tellurium metal (Te). The two-dimensional array depicted in FIG. 3 summarizes these experiments. Note in particular the result for about 2.5 mol % Te and 5 mol % $Bi(NO_3)_3.5H_2O$, which enabled a 94% yield of methyl octanoate.

Re-examination of other palladium sources at 1 mol % Pd loading with the optimized $Bi(NO_3)_3.5H_2O$/Te combinations showed that comparable results could be obtained with 2.5% or 5% Pd/C. The somewhat lower cost of Pd/Char prompted us to proceed with this catalyst.

A more robust catalyst was also developed in which the bismuth and tellurium were deposited onto the palladium prior to reaction in a preferred molar ratio of Pd:Bi:Te of 1:0.35:0.23. This catalyst added the benefit of being able to be recycled through multiple reactions or of being able to be used in a continuous process.

Figure 4:
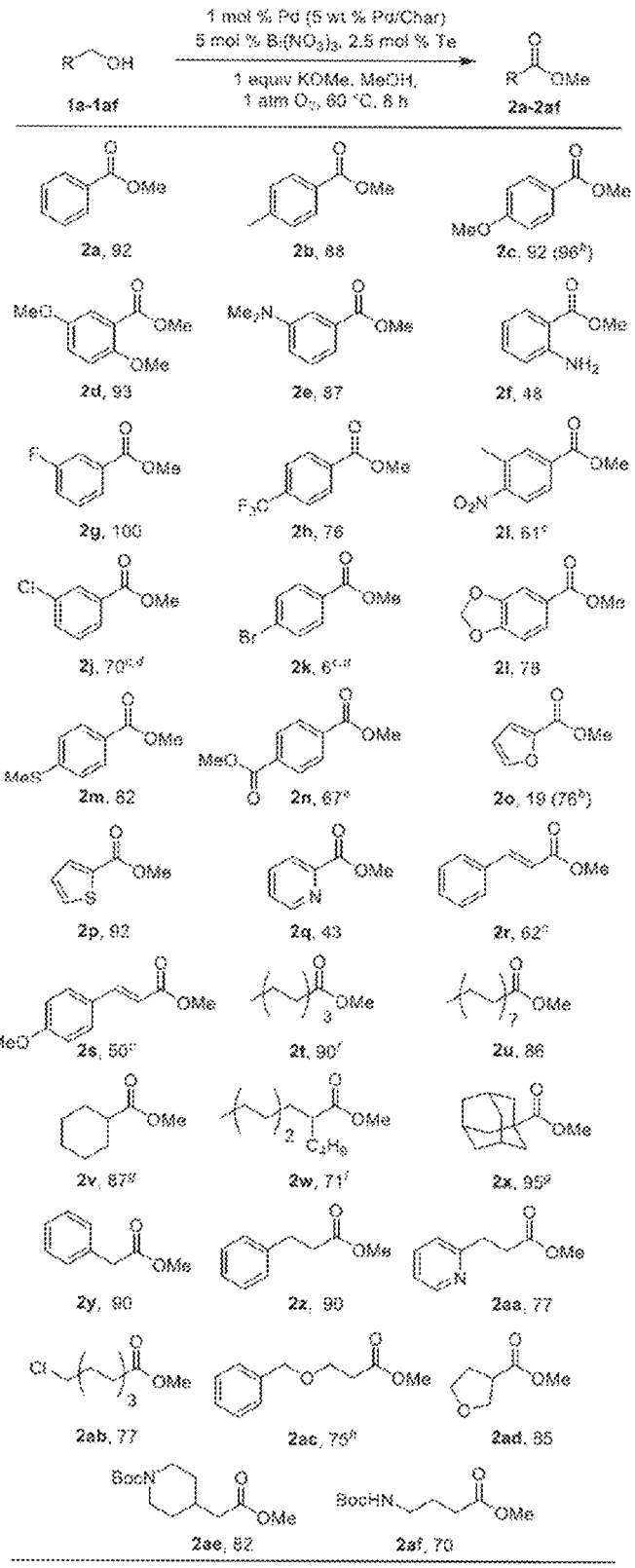
FIG. 4 depicts various methyl esters formed by the methods of the present invention.

We then ran a series of experiments on other alcohol substrates, at various temperatures. See generally FIGS. 4 and 5. While a variety of temperature conditions were appropriate, a temperature of about 60° C. proved very desirable.

We then tested the use of such catalysts for converting the alcohol substrate to an acid in the presence of water. We therefore also describe below the application of our catalysts for the aerobic oxidation of primary alcohols, benzylic, cyclic and aliphatic, to the corresponding carboxylic acids.

Figures 6, 7:
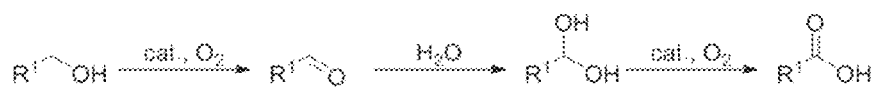
FIG. 6 provides a generic representation of the methods of the present invention as applied to formation of carboxylic acids.
FIG. 7 depicts a number of specific examples of substrates used for formation of carboxylic acids.

In FIGS. 6 and 7 we depict proof of principle examples of oxidizing alcohols to carboxylic acids.

DETAILED EXPERIMENTS

We provide below more details regarding the experiments summarized above:

Commercially available compounds were used as received and purchased from Sigma Aldrich unless otherwise indicated. Pd sources from Sigma Aldrich (# product number) included 1 wt % Pd/C (205672), 1 wt % Pd/$Al_2O_3$ (205702), 2.5 wt % Pd/C (276707), 5 wt % Pd/C (520845), 5 wt % Pd/charcoal (75992), 30 wt % Pd/C (407305), $PdCl_2$ (205885) and Pd(OAc)$_2$ (520764). A 5 wt % Pd/C catalyst was also obtained from TCI Chemicals (P1490).

The bismuth(III) nitrate pentahydrate used (Bi(NO$_3$)$_3$.5H$_2$O) and Te metal were purchased from Sigma Aldrich. A substrate CAS Number 17581-85-0 was purchased from Matrix Scientific. $^1$H and $^{13}$C NMR spectra were recorded on a Bruker AC-400 MHz spectrometer. The chemical shifts (δ) were recorded in parts per million and referenced to trimethyl(phenyl)silane (PhTMS) internal standard. High resolution mass spectra were obtained using a Water Autospec by the mass spectrometry facility at the University of Wisconsin. Infrared measurements were acquired on a Bruker Tensor 27 FTIR with an ATR probe as neat samples. Melting points were taken on a Mel-Temp II melting point apparatus. Flash column chromatography was performed using silica gel 60 (Silicycle) and eluted with ethyl acetate/hexanes.

A 4 L screw top bottle of anhydrous methanol was used. Base: KOMe was added as a 3.75 M MeOH solution from Sigma Aldrich, or K$_2$CO$_3$ (from Sigma Aldrich) was added as a solid or dissolved in methanol.

We took particular caution in handling these materials because the addition of neutral methanol to Pd/Charcoal can cause the Pd to catch fire. Unless otherwise stated the KOMe was delivered to the Pd/Charcoal as a 3.75 M solution in MeOH. In this regard the Pd/Charcoal will not combust upon the addition of KOMe in methanol. The robust Pd$_x$-Bi$_y$Te$_z$/C catalysts proved not to be flammable with the addition of methanol.

We also considered that some methyl ester products with boiling points near/below 200° C. (2a, 2p, 2t, 2z, 2ad of FIG. 6) can be lost to evaporation on a strong rotary evaporator (~30 mm Hg vacuum) over prolonged periods of time. In these cases an aqueous workup of the crude reaction mixture with DI water/CH$_2$Cl$_2$ is preferable because CH$_2$Cl$_2$ is rapidly removed upon rotary evaporation leaving the pure methyl ester behind. Purification by column chromatography with hexanes and ethyl acetate usually requires prolonged exposure to reduced pressure, which may result in the loss of some product.

We made one of our catalysts as follows. 500 mg of 5 wt. % Pd on carbon was added to 15 mL of distilled water and stirred. Bi(NO$_3$)$_3$.5H$_2$O and TeCl$_4$ was dissolved in a mixture of 1 mL 1 M HCl and 0.1 mL conc. HNO$_3$ and added to the catalyst suspension. The Pd/C and dissolved salts were mixed at 50° C. for 3 hours. After the 3 hours 500 µL of a 30% NaOH solution was added to make the mixture alkaline. 200 µL of 37% formaldehyde was then added and the mixture heated to 80° C. under N$_2$. The catalyst was then allowed to reduce over 16 hours after which it was filtered and washed with water (~500 mL) until neutral. The catalyst was then dried under vacuum at 70° C. for 20 hours to afford the final catalyst PdBi$_{0.35}$Te$_{0.23}$/C.

General Procedure

To a disposable 13 mm thick-walled culture tube was added the reaction components. For example, we added 5 wt % Pd/Charcoal (0.01 mmol, 21.3 mg), tellurium metal (0.025 mmol, 3.2 mg), 3.75 M KOMe in MeOH (1 mmol, 0.27 mL), 0.25 M trimethoxybenzene in MeOH (as an internal standard, 0.40 mL), 0.5 M Bi(NO$_3$)$_3$.5H$_2$O in MeOH (0.10 mL) and 0.07 mL MeOH. The reaction tubes were then placed in a 48-well parallel reactor mounted on a Glas-Col large capacity mixer. With the robust catalyst PdBi$_{0.35}$Te$_{0.23}$/C (0.01 mmol, 21.3 mg, 5 wt. % Pd), K$_2$CO$_3$ (0.25 mmol, 34.6 mg), and MeOH were added to the reaction tubes.

The headspace was purged with O$_2$ for about 3 minutes, heated to the appropriate temperature and the alcohol substrates (1 mmol) were injected into each vial. The reactions were shaken at elevated temperature under 1 atmosphere O$_2$ for 12 hour, after which time they were stopped and filtered through celite plugs. The plugs were washed with MeOH, CH$_2$Cl$_2$ and MeOH, and concentrated in vacuuo.

Trimethyl(phenyl)silane (0.5 mmol, 86 µL) was added and the reactions were analyzed by $^1$H NMR spectroscopy. Yields for each reaction were quantified by comparison of the products with both trimethoxybenzene (0.1 mmol) and trimethyl(phenyl)silane (0.5 mmol).

Aerobic Alcohol Esterification with Orbital Mixer (Conditions A)

This set of reactions was carried out in a 13 mm thick-walled culture tubes under 1 atmosphere O$_2$ with agitation provided by an orbital shaker as described in the paragraph above. To each of the tubes was charged with 5 wt % Pd/Charcoal (0.01 mmol, 21.3 mg), tellurium metal (0.025 mmol, 3.2 mg), 3.75 M KOMe in MeOH (1.0 mmol, 0.27 mL), MeOH (0.40 mL), 0.5 M Bi(NO$_3$)$_3$.5H$_2$O in MeOH (0.10 mL) and 0.07 mL MeOH. The tubes were placed in a 48-well parallel reactor mounted on a Glas-Col large capacity mixer. The head space was purged with O$_2$ for about 3 min, and the reactions were then heated to 60° C. unless otherwise indicated.

The alcohol substrate was added via syringe (1 mmol) or as a solution in MeOH for solid substrates. The reactions were allowed to react at 60° C. under 1 atmosphere O$_2$ for 8 hours unless otherwise indicated. The reactions were then filtered through celite plugs, washed with MeOH, CH$_2$Cl$_2$ and MeOH and concentrated in vacuuo. The residue was loaded on the top of a silica gel column and the product was isolated by elution with hexanes/EtOAc.

Aerobic Alcohol Esterification with O$_2$ Balloon (Conditions B)

A 20 mm×150 mm culture tube was charged with a stir bar, 5 wt % Pd/Charcoal (0.01 mmol, 21.3 mg), tellurium metal (0.025 mmol, 3.2 mg), 3.75 M KOMe in MeOH (0.27 mL), MeOH (0.40 mL), 0.5 M Bi(NO$_3$)$_3$.5H$_2$O in MeOH (0.10 mL) and 0.07 mL MeOH. The tube was stoppered with a rubber septum and the solution was purged with O$_2$ saturated MeOH for 10 min. An O$_2$ balloon was attached to a 16" gauge needle (12" long) and the needle was placed through the septum of the tube so that the needle was submerged into the solution. The culture tube was warmed to 50° C., after which the substrate (1 mmol) was injected into the vial and the reaction was stirred rapidly at 800 rpm for 8 hour. The reactions were then filtered through celite plugs, washed with MeOH, CH$_2$Cl$_2$ and MeOH and concentrated in vacuuo. The residue was loaded on the top of a silica gel column and the product was isolated by elution with hexanes/EtOAc.

For continuous production a packed bed reactor was made consisting of 350 mg PdBi$_{0.35}$Te$_{0.23}$/C in a 4 inch long ¼ inch outer diameter stainless steel tube. O$_2$ was fed as a dilute mixture in N$_2$ (9% O$_2$) with a molar flow rate of O$_2$:substrate of 8:1 and O$_2$ pressure of 0.5 atmospheres. The substrate was fed as a 5M solution in MeOH and the K$_2$CO$_3$ was fed as a 0.138 M solution in MeOH. The liquid feeds were mixed with the gas feed before the reactor giving a final solution of 0.5 M substrate and 0.125 M K$_2$CO$_3$ in MeOH. Samples were collected and analyzed by GC with mesitylene as a standard.

Spectral Data for Isolated Methyl Esters

With reference to the esters referred to in FIG. 6, we achieved the following results for various benzyl and alkyl alcohols:

2a Yield: 92%. Colorless oil. Purified by silica gel column chromatography using 9:1 hexanes: EtOAc ($R_f$=0.45). $^1$H NMR (400 MHz, CDCl$_3$, TMS) δ 8.04 (d, J=7.1 Hz, 2H), 7.59-7.51 (m, 1H), 7.43 (t, J=7.8 Hz, 2H), 3.91 (s, 3H).

2b Yield: 88%. Colorless oil. Purified by silica gel column chromatography using 9:1 hexanes: EtOAc ($R_f$=0.55). $^1$H NMR (400 MHz, CDCl$_3$, TMS) δ 7.92 (d, J=8.2 Hz, 2H), 7.22 (dd, J=8.4, 0.9 Hz, 2H), 3.88 (s, 3H), 2.39 (s, 3H).

2c Yield: 92%. Colorless oil. Purified by silica gel column chromatography using 8:2 hexanes: EtOAc ($R_f$=0.40). $^1$H NMR (400 MHz, CDCl$_3$, TMS) δ 7.99 (d, J=8.9 Hz, 2H), 6.91 (d, J=8.9 Hz, 2H), 3.87 (s, 3H), 3.84 (s, 3H).

2d Yield: 93%. Colorless oil. Purified by silica gel column chromatography using 6:4 hexanes: EtOAc (Rf=0.48). $^1$H NMR (400 MHz, CDCl$_3$, TMS) δ 7.36-7.31 (m, 1H), 7.05-6.98 (m, 1H), 6.96-6.86 (m, 1H), 3.89 (s, 3H), 3.85 (s, 3H), 3.78 (s, 3H).

2e Yield: 87%. Colorless oil. Purified by silica gel column chromatography using 8:2 hexanes: EtOAc ($R_f$=0.40). $^1$H NMR (400 MHz, CDCl$_3$, TMS) δ 7.43-7.35 (m, 2H), 7.28 (t, J=7.9 Hz, 1H), 6.90 (dd, J=2.6, 1.1 Hz, 1H), 3.90 (s, 3H), 2.98 (s, 6H).

2f Yield: 48%. Colorless oil. Purified by silica gel column chromatography using 9:1 hexanes: EtOAc (Rf=0.21). $^1$H NMR (400 MHz, CDCl$_3$, TMS) δ 7.85 (ddd, J=7.7, 1.6, 0.7 Hz, 1H), 7.25 (ddd, J=8.6, 7.2, 1.6 Hz, 1H), 6.70-6.60 (m, 2H), 5.71 (s, 2H), 3.86 (s, 3H).

2g Yield: 100%. Colorless oil. Purified by silica gel column chromatography using 9:1 hexanes: EtOAc ($R_f$=0.41). $^1$H NMR (400 MHz, CDCl$_3$, TMS) δ 7.83 (dd, J=7.8, 1.4 Hz, 1H), 7.75-7.66 (m, 1H), 7.40 (ddd, J=8.0, 5.1, 3.1 Hz, 1H), 7.31-7.17 (m, 1H), 3.92 (d, J=1.6 Hz, 3H).

2h Yield: 76%. Colorless oil. Purified by silica gel column chromatography using 9:1 hexanes: EtOAc ($R_f$=0.40). $^1$H NMR (400 MHz, CDCl$_3$, TMS) δ 8.15 (d, J=8.0 Hz, 2H), 7.70 (d, J=8.1 Hz, 2H), 3.96 (d, 3H).

2i Yield: 61%. Orange solid. Reacted at 25° C. for 8 hours. Purified by silica gel column chromatography using 8:2 hexanes: EtOAc ($R_f$=0.40). $^1$H NMR (400 MHz, CDCl$_3$, TMS) δ 8.02 (dt, J=1.7, 0.8 Hz, 1H), 7.97 (dd, J=2.1, 1.2 Hz, 2H), 3.97 (s, 3H), 2.62 (d, J=0.9 Hz, 3H). $^{13}$C NMR (101 MHz, CDCl$_3$, TMS) δ 165.30, 151.84, 133.99, 133.73, 133.46, 128.05, 124.56, 52.73, 20.07. HRMS (EI) Calcd. for C$_9$H$_9$NO$_4$ ([M$^+$]): 195.0527, found: 195.0526. IR (cm$^{-1}$): 1728, 1516, 1429, 1279, 1263, 1198, 1122, 982, 836, 731. M.P. 80-82° C.

2j Yield: 65%. Colorless oil. Isolated with 33% methyl benzoate. Reacted for 25° C. for 8 hours. Purified by silica gel column chromatography using 9:1 hexanes: EtOAc ($R_f$=0.42). $^1$H NMR (400 MHz, CDCl$_3$, TMS) δ 8.00 (t, J=1.9 Hz, 1H), 7.91 (dt, J=7.8, 1.3 Hz, 1H), 7.51 (ddd, J=8.1, 2.3, 1.2 Hz, 1H), 7.42 (dd, J=8.4, 7.1 Hz, 1H), 3.91 (d, J=1.4 Hz, 3H).

2k Yield: 6%. Colorless oil. Isolated with 20% methyl benzoate. Reacted for 25° C. for 8 hours. Purified by silica gel column chromatography using 9:1 hexanes: EtOAc ($R_f$=0.42). $^1$H NMR (400 MHz, CDCl$_3$, TMS) δ 7.90 (d, J=8.0 Hz, 2H), 7.48 (d, J=8.5 Hz, 2H), 3.92 (s, 3H).

2l Yield: 78%. White solid. Purified by silica gel column chromatography using 8:2 hexanes: EtOAc ($R_f$=0.55). $^1$H NMR (400 MHz, CDCl$_3$, TMS) δ 7.63 (dd, J=8.2, 1.7 Hz, 1H), 7.45 (d, J=1.7 Hz, 1H), 6.82 (d, J=8.2 Hz, 1H), 6.02 (s, 2H), 3.87 (s, 3H). $^{13}$C NMR (101 MHz, CDCl$_3$, TMS) δ 166.43, 151.57, 147.71, 125.31, 124.16, 109.49, 107.94, 101.79, 52.04. HRMS (EI) Calcd. for C$_9$H$_8$O$_4$ ([M$^+$]): 180.0418, found: S15 180.0424. IR (cm$^{-1}$): 1725, 1712, 1502, 1444, 1282, 1269, 1160, 1110, 1078, 1037, 931, 898, 756. M.P. 51-53° C.

2m Yield: 82%. White solid. Purified by silica gel column chromatography using 9:1 hexanes: EtOAc ($R_f$=0.37). $^1$H NMR (400 MHz, CDCl$_3$, TMS) δ 7.92 (d, J=8.5 Hz, 2H), 7.23 (d, J=8.5 Hz, 2H), 3.89 (s, 3H), 2.50 (s, 3H).

2n Yield: 67%. White solid. Purified by silica gel column chromatography using 8:2 hexanes: EtOAc ($R_f$=0.42). $^1$H NMR (400 MHz, CDCl$_3$, TMS) δ 8.09 (s, 4H), 3.94 (s, 6H).

2o Yield: 76%. Colorless oil. Purified by silica gel column chromatography using 8:2 hexanes: EtOAc ($R_f$=0.39). $^1$H NMR (400 MHz, CDCl$_3$, TMS) δ 7.58 (td, J=1.8, 0.9 Hz, 1H), 7.18 (ddd, J=3.2, 2.0, 0.9 Hz, 1H), 6.51 (dd, J=3.5, 1.8 Hz, 1H), 3.90 (d, J=2.2 Hz, 3H).

2p Yield: 92%. Colorless oil. Purified by silica gel column chromatography using 8:2 hexanes: EtOAc ($R_f$=0.53). $^1$H NMR (400 MHz, CDCl$_3$, TMS) δ 7.80 (dd, J=3.8, 1.3 Hz, 1H), 7.55 (dd, J=5.0, 1.3 Hz, 1H), 7.10 (dd, J=5.0, 3.7 Hz, 1H), 3.89 (s, 3H).

2q Yield: 43%. Colorless oil. Purified by silica gel column chromatography using 100% EtOAc ($R_f$=0.40). $^1$H NMR (400 MHz, CHCl$_3$, TMS) δ 8.76 (ddd, J=4.8, 1.8, 0.9 Hz, 1H), 8.15 (dt, J=7.8, 1.0 Hz, 1H), 7.86 (td, J=7.7, 1.7 Hz, 1H), 7.50 (ddd, J=7.6, 4.7, 1.2 Hz, 1H), 4.02 (s, 3H).

2r Yield: 62%. Colorless oil. Reacted at 25° C. for 8 hours. Purified by silica gel column chromatography using 9:1 hexanes: EtOAc ($R_f$=0.41). $^1$H NMR (400 MHz, CDCl$_3$, TMS) δ 7.69 (d, J=16.0 Hz, 1H), 7.58-7.45 (m, 2H), 7.41-7.32 (m, 3H), 6.43 (d, J=16.0 Hz, 1H), 3.78 (s, 3H).

2s Yield: 50%. Reacted at 25° C. for 8 hours. White solid. Purified by silica gel column chromatography using 85:15 hexanes: EtOAc ($R_f$=0.28). $^1$H NMR (400 MHz, CDCl$_3$, TMS) δ 7.65 (d, J=16.0 Hz, 1H), 7.46 (d, J=8.7 Hz, 2H), 6.89 (d, J=8.7 Hz, 2H), 6.30 (d, J=16.0 Hz, 1H), 3.78 (s, 6H).

2t Yield: 90%. Colorless oil. Reacted at 60° C. for 15 hours. Purified by silica gel column chromatography using 9:1 hexanes: EtOAc ($R_f$=0.65). $^1$H NMR (400 MHz, CDCl$_3$, TMS) δ 3.67 (s, 3H), 2.30 (t, J=7.6 Hz, 2H), 1.63 (q, J=7.2, 6.4 Hz, 2H), 1.29 (qd, J=7.0, 5.3, 3.0 Hz, 8H), 0.91-0.84 (m, 3H).

2u Yield: 86%. Colorless oil. Purified by silica gel column chromatography using 9:1 hexanes: EtOAc ($R_f$=0.65). $^1$H NMR (400 MHz, CDCl3, TMS) δ 3.66 (s, 3H), 2.30 (t, J=7.6 Hz, 2H), 1.62 (t, J=7.3 Hz, 2H), 1.27 (d, J=10.5 Hz, 24H), 0.88 (t, J=6.8 Hz, 3H). $^{13}$C NMR (101 MHz, CDCl$_3$, TMS) δ 174.31, 51.42, 31.97, 29.73, 29.71, 29.70, 29.69, 29.64, 29.41, 29.30, 22.73, 14.14. HRMS (EI) Calcd. for C$_{16}$H$_{34}$O$_2$ ([M$^+$]): 270.2554, found: 270.2553. IR (cm$^{-1}$): 2917, 2849, 1740, 1463, 1220, 1198, 1174, 730, 720.

2v Yield: 87%. Colorless oil. Reacted at 70° C. for 8 hours. Purified by silica gel column chromatography using 9:1 hexanes: EtOAc ($R_f$=0.60). $^1$H NMR (400 MHz, CDCl$_3$, TMS) δ 3.66 (s, 3H), 2.30 (ddt, J=11.3, 7.4, 3.6 Hz, 1H), 1.97-1.84 (m, 2H), 1.82-1.69 (m, 2H), 1.69-1.60 (m, 1H), 1.50-1.37 (m, 2H), 1.36-1.16 (m, 3H).

2w Yield: 77%. Colorless oil. Reacted at 60° C. for 15 hours. Purified by silica gel column chromatography using 95:5 hexanes: EtOAc ($R_f$=0.26). $^1$H NMR (400 MHz, CDCl$_3$, TMS) δ 3.67 (s, 3H), 2.43-2.24 (m, 1H), 1.70-1.53 (m, 2H), 1.45 (dd, J=7.6, 5.1 Hz, 2H), 1.38-1.16 (m, 12H), 0.97-0.79 (m, 6H). $^{13}$C NMR (101 MHz, S17 CDCl$_3$, TMS) δ 177.10, 51.28, 45.75, 32.58, 32.28, 31.74, 29.72, 29.27, 22.68, 22.63, 14.08, 13.97. HRMS (EI) Calcd. for C$_{13}$H$_{26}$O$_2$ ([M+]): 214.1850, found: 214.1842. IR (cm$^{-1}$): 2956, 2930, 2859, 1738, 1459, 1193, 1164, 733.

2x Yield: 95%. Colorless solid. Reacted at 70° C. for 8 hours. Purified by extraction from DI water (50 mL) with CH$_2$Cl$_2$ (3×25 mL). $^1$H NMR (400 MHz, CDCl$_3$, TMS) δ 3.65 (s, 3H), 2.07-1.96 (m, 3H), 1.89 (d, J=3.1 Hz, 6H), 1.71 (dt, J=4.3, 2.3 Hz, 6H).

2y Yield: 90%. Colorless oil. Purified by silica gel column chromatography using 9:1 hexanes: EtOAc (R$_f$=0.38). $^1$H NMR (400 MHz, CDCl$_3$, TMS) δ 7.36-7.22 (m, 5H), 3.67 (s, 3H), 3.61 (s, 2H).

2z Yield: 90%. Colorless oil. Purified by silica gel column chromatography using 8:2 hexanes: EtOAc (R$_f$=0.50). $^1$H NMR (400 MHz, CDCl$_3$, TMS) δ 7.32-7.23 (m, 2H), 7.22-7.14 (m, 3H), 3.65 (s, 3H), 2.94 (t, J=7.9 Hz, 2H), 2.62 (dd, J=8.4, 7.3 Hz, 2H).

2aa Yield: 77%. Colorless oil. Purified by silica gel column chromatography using 4:6 hexanes: EtOAc (R$_f$=0.34). $^1$H NMR (400 MHz, CDCl$_3$, TMS) δ 8.52 (d, J=3.1 Hz, 1H), 7.58 (td, J=7.7, 1.8 Hz, 1H), 7.18 (d, J=7.8 Hz, 1H), 7.14-7.07 (m, 1H), 3.66 (s, 3H), 3.12 (t, J=7.5 Hz, 2H), 2.82 (t, J=7.5 Hz, 2H).

2ab Yield: 77%. Colorless oil. Purified by silica gel column chromatography using 95:5 hexanes: EtOAc (R$_f$=0.32). $^1$H NMR (400 MHz, CDCl$_3$, TMS) δ 3.67 (s, 3H), 3.53 (t, J=6.7 Hz, 2H), 2.31 (t, J=7.5 Hz, 2H), 1.84-1.70 (m, 2H), 1.63 (ddd, J=7.3, 4.8, 2.5 Hz, 2H), 1.39-1.32 (m, 6H). $^{13}$C NMR (101 MHz, CDCl$_3$, TMS) δ 174.14, 51.45, 45.05, 34.01, 32.55, 28.96, 28.54, 26.69, 24.83. HRMS (EI) Calcd. for C$_9$H$_{17}$ClO$_2$ ([M+]): 192.0912, found: 192.0911. IR (cm$^{-1}$): 2935, 2859, 1738, 1694, 1436, 1365, 1244, 1196, 1171, 1094, 1014, 916, 838, 731. S18.

2ac Yield: 75%. Colorless oil. Reacted at 50° C. for 12 hours. Purified by silica gel column chromatography using 85:15 hexanes: EtOAc (R$_f$=0.50). $^1$H NMR (400 MHz, CDCl$_3$, TMS) δ 7.41-7.21 (m, 5H), 4.53 (s, 2H), 3.74 (t, J=6.4 Hz, 2H), 3.68 (s, 3H), 2.61 (t, J=6.4 Hz, 2H).

2ad Yield: 85%. Colorless oil. Purified by silica gel column chromatography using 90:10 hexanes: EtOAc (R$_f$=0.40). $^1$H NMR (400 MHz, CDCl$_3$, TMS) δ 4.04-3.76 (m, 4H), 3.71 (s, 3H), 3.10 (ddt, J=9.1, 8.0, 6.2 Hz, 1H), 2.30-2.00 (m, 2H). $^{13}$C NMR (101 MHz, CDCl$_3$) δ 174.28, 70.31, 68.25, 52.04, 43.68, 29.57. HRMS (EI) Calcd. for C$_6$H$_{10}$O$_3$ ([M+]): 130.0625, found: 130.0627. IR (cm$^{-1}$): 2955, 2867, 1734, 1437, 1356, 1202, 1174, 1069, 1023, 920.

2ae Yield: 82%. Colorless oil. Purified by silica gel column chromatography using 8:2 hexanes: EtOAc (R$_f$=0.32). $^1$H NMR (400 MHz, CDCl$_3$, TMS) δ 4.41-3.89 (m, 2H), 3.67 (s, 3H), 2.93-2.59 (m, 2H), 2.25 (d, J=7.1 Hz, 2H), 1.93 (ddd, J=11.4, 7.6, 4.0 Hz, 1H), 1.80-1.62 (m, 2H), 1.45 (s, 9H), 1.16 (tt, J=12.4, 6.2 Hz, 2H). $^{13}$C NMR (101 MHz, CDCl$_3$, TMS) δ 172.77, 154.74, 79.28, 51.46, 43.72, 40.84, 33.06, 31.80, 28.43. HRMS (ESI) Calcd. for C$_{13}$H$_{23}$NO$_4$ ([M+H+]): 258.1700, found: 258.1695. IR (cm$^{-1}$): 1738, 1692, 1422, 1366, 1288, 1240, 1159, 1121, 1014, 733.

2af Yield: 70%. Colorless oil. Purified by silica gel column chromatography using 7:3 hexanes: EtOAc (R$_f$=0.50). $^1$H NMR (400 MHz, CDCl$_3$, TMS) δ 4.83 (s, 1H), 3.68 (s, 3H), 3.16 (q, J=6.7 Hz, 2H), 2.36 (t, J=7.4 Hz, 2H), 1.91-1.72 (m, 2H), 1.44 (s, 9H).

We also experimented with adding lead, cerium, titanium, zinc, and/or niobium as an additional co-catalyst, with positive results. Of these, lead was the most promising.

Formation of the Acid (Condition C)

Figure 8:
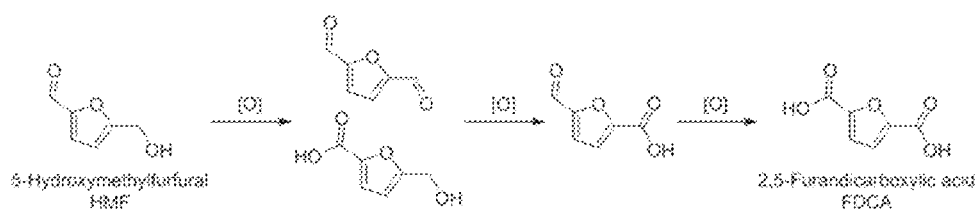
FIG. 8 focuses on a specific example of formation of a cyclic carboxylic acid.
Figure 9:
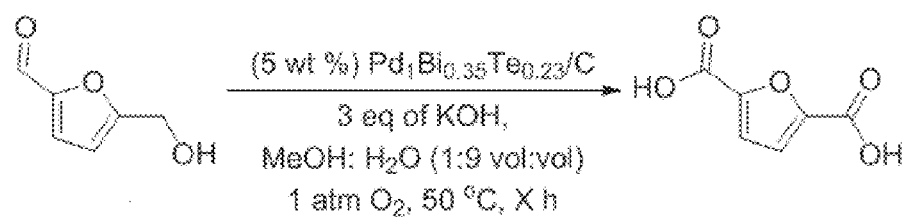
FIG. 9 depicts further details regarding reaction conditions.
Figure 10:
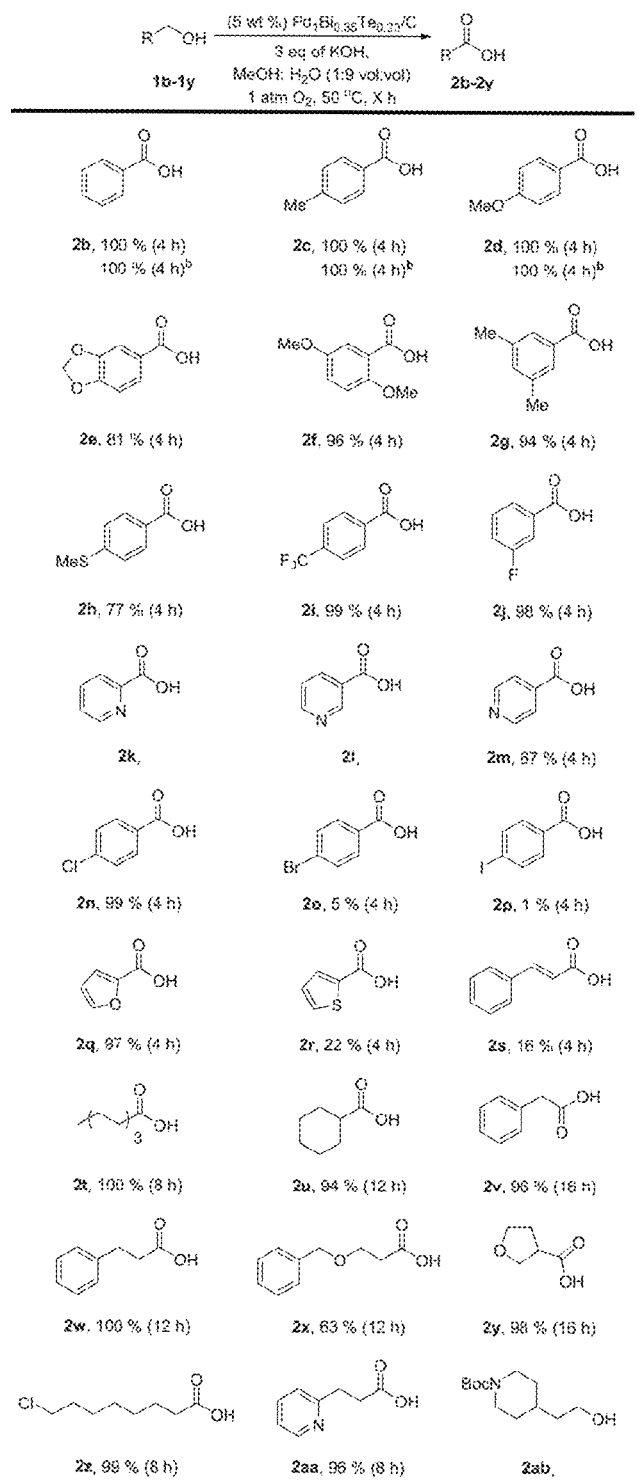
FIG. 10 depicts other carboxylic acids formed under the conditions specified.

A typical acid synthesis added the alcohol substrate to about three equivalents of a base such as KOH, in a solvent like MeOH:H$_2$O (1:9 vol/vol), under about 1 atmosphere O$_2$, at about 50° C. for about 4 hours. As one example we converted 5-hydroxymethylfurfural to 2,5-furandicarboxylic acid, per FIG. 8 under the conditions of FIG. 9. FIG. 10 also depicts a variety of other starting substrates that we converted to the acid form using our invention.

EXAMPLES

The examples presented below include additional details and extensions of the disclosed methods.

Example 1: PdBiTe Catalysts for Aerobic Oxidative Esterification of Primary Alcohols This example highlights the potential of "admixture screening" as an efficient method for the discovery of new heterogeneous catalyst compositions, and the method is illustrated in the development of robust heterogeneous Pd catalysts for aerobic oxidative methyl esterification of primary alcohols. The identification of possible catalysts for this reaction was initiated by the screening of simple binary and ternary admixtures of Pd/charcoal in combination with one or two metal and/or metalloid components as the catalyst. This approach permitted rapid evaluation of over 400 admixture combinations for the oxidative methyl esterification of 1-octanol at 60° C. in methanol. Product yields from these reactions varied widely, ranging from 2-88%. The highest yields were observed with Bi-, Te and Pb-based additives, and particularly from those containing both Bi and Te. Validation of the results was achieved by preparing specific PdBiTe catalyst formulations via a wet-impregnation method, followed by application of response surface methodology to identify the optimal Pd—Bi—Te catalyst stoichiometry. This approach revealed two very effective catalyst compositions: PdBi$_{0.47}$Te$_{0.09}$/C (PBT-1) and PdBi$_{0.35}$Te$_{0.23}$/C (PBT-2). The former catalyst was used in batch aerobic oxidation reactions with different primary alcohols and shown to be compatible with substrates bearing heterocycle and halide substituents. The methyl ester products were obtained in >90% yield in each case. Implementation of the PBT-2 catalyst in a continuous-flow packed-bed reactor achieved nearly 60,000 turnovers with no apparent loss of catalytic activity.

Introduction

Heterogeneous catalysts offer numerous potential advantages over homogeneous catalysts for the industrial synthesis of organic chemicals.[1] Their thermal stability and ease of catalyst immobilization (e.g., in fixed-bed or other reactor configurations) are particularly advantageous for high-temperature, gas-phase and large-volume continuous processes in the commodity chemical industry. Contemporary heterogeneous catalyst development efforts are especially focused on such applications. Heterogeneous catalysts also have benefits for lower-volume production of pharmaceuticals and fine chemicals; however, the development of catalysts that exhibit the broad functional group tolerance needed in applications of this type have been the focus of much less attention. One potential barrier to progress in this area is that the synthetic organic and organometallic chemistry background of many researchers within the pharmaceutical and related industries provides little or no training in the synthesis or characterization of heterogeneous catalysts and materials. Experimental strategies that lower the barrier to heterogeneous catalyst discovery and development could significantly expand the application of heterogeneous catalysts in these industries.

Heterogeneous catalysts for organic chemical processes are typically composed of an active metal dispersed on a support material, such as high-surface-area carbon, a metal oxide, or other inorganic material. Many catalysts also feature "promoters" that modulate the activity or selectivity of the metal catalyst.[2] A prominent example is Lindlar's catalyst for partial reduction of alkynes to alkenes, which consists of $CaCO_3$-supported Pd in combination with Pb and quinoline as selective modifiers or poisons to prevent full reduction of the alkyne to the saturated C—C bond.[3] Heterogeneous catalysts are commonly prepared through the deposition of the active metal and promoters onto a support via one of numerous possible methods, including impregnation, adsorption, precipitation, or ion exchange.[4] Additional washing, drying, and calcination steps are typically incorporated as intermediate or final steps to prepare the ultimate catalyst. The sequential steps employed in catalyst preparation, which are often viewed as integral to the catalyst performance, can be labor- and/or time-intensive. High-throughput methods have been developed to improve the pace of catalyst preparation and analysis of their activity;[5,6] however, these methods typically still rely on independent one-by-one synthesis and formulation of individual catalysts.

Heterogeneous Pd and Pt catalysts have been studied extensively for aerobic oxidation of primary and secondary alcohols to carboxylic acids, ketones, and aldehydes.[7] The incorporation of one or more promoters derived from the early transition metals, lanthanides, and/or main group elements often enhances the catalyst activity and selectivity.[8] The origin of the promoter effects is often not fully understood, but previous studies implicate contributions ranging from selective blocking of catalyst sites that lead to side reactions[8a,k-m] to the formation of synergistic catalyst/promoter active sites that enhance catalyst performance.[8c,h,i] Promoters may form surface alloys or intermetallic structures that exhibit different activity relative to the pure-metal catalyst or hinder agglomeration of metal nanoparticles.[8d,g,p] And, some promoters are believed to mediate adsorption and dissociation of $O_2$, thereby protecting the catalytic metal surface from over-oxidation.[8f,k-m] The diverse roles of individual promoters and the potential for synergistic interactions between promoters complicate the rational design of new heterogeneous catalysts, but they also represent an important modular feature of the catalysts that can be altered to optimize catalyst performance, similar to the manner in which ancillary ligands may be used to modulate the activity and/or selective of homogeneous catalysts.

In this example, we describe a readily accessible "admixture screening" method that streamlines the assessment and identification of effective heterogeneous catalyst/promoter combinations. We further show that catalysts discovered by this method serve as useful starting points for the development of robust multicomponent catalysts suitable for implementation in a continuous flow process relevant to pharmaceutical or other specialty chemical applications. These principles are illustrated in the development of heterogeneous Pd/Bi/Te catalysts for oxidative methyl esterification of primary alcohols, including those bearing heterocycles and halide substituents.

Results and Discussion

Context and Preliminary Results.

Previous studies by us[9] and others[10] have investigated homogeneous Pd catalysts for aerobic oxidation of alcohols to aldehydes and ketones. Whereas numerous useful catalysts have been identified for these two-electron oxidation reactions, development of analogous homogeneous catalysts for four-electron oxidation of primary alcohols to carboxylic acids and esters has been less successful.[11] In contrast, heterogeneous catalysts show significant promise for the latter applications.[7] The oxidative cross-coupling of primary alcohols with methanol (Scheme 1) is a particularly useful transformation that provides a means to reverse the polarity of nucleophilic primary alcohols into electrophilic methyl esters.

Scheme 1. Generic Pathway for the
Aerobic Oxidation of Alcohols to Methyl Esters.

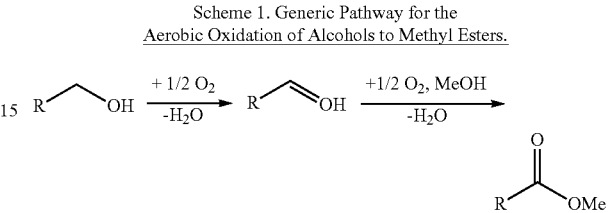

Gas-phase oxidative methyl esterification of aliphatic alcohols has been demonstrated with Au-based catalysts,[12] and liquid-phase precedents have been achieved with supported Ag[13] and Au,[14] polymer-incarcerated mixed noble-metal nanoparticles,[15] and heterogeneous cobalt catalysts.[16] Precedents for heterogeneous Pd catalysts for the oxidation of primary alcohols to carboxylic acids.[8d-g,i,j,n-p] suggested to us that related catalysts could be highly effective for oxidative methyl esterification and may show good compatibility with alcohols bearing diverse functional groups. These catalysts often incorporate main-group promoters that enhance the catalytic performance. In a recent preliminary study, we found that Pd/charcoal (5 wt. %) is an effective catalyst for methyl esterification of a variety of primary alcohols when $Bi(NO_3)_3.5H_2O$ and Te metal are included as co-catalysts (5 mol % each) in the batch reaction mixtures.[17,18] This admixture catalyst system exhibited excellent activity and functional-group compatibility.

Admixture Screening Studies.

The heterogeneous catalyst system just noted is poorly defined: the sources of promoters, $Bi(NO_3)_3.5H_2O$ and Te, exhibit poor solubility in the methanol solvent, and the nature of the interactions between the promoters and the heterogeneous Pd catalyst was not characterized. In spite of these complexities and uncertainties, the promising results raised the possibility that simple catalyst admixtures could be used in primary screening studies to discover new heterogeneous catalysts.

Figure 11:
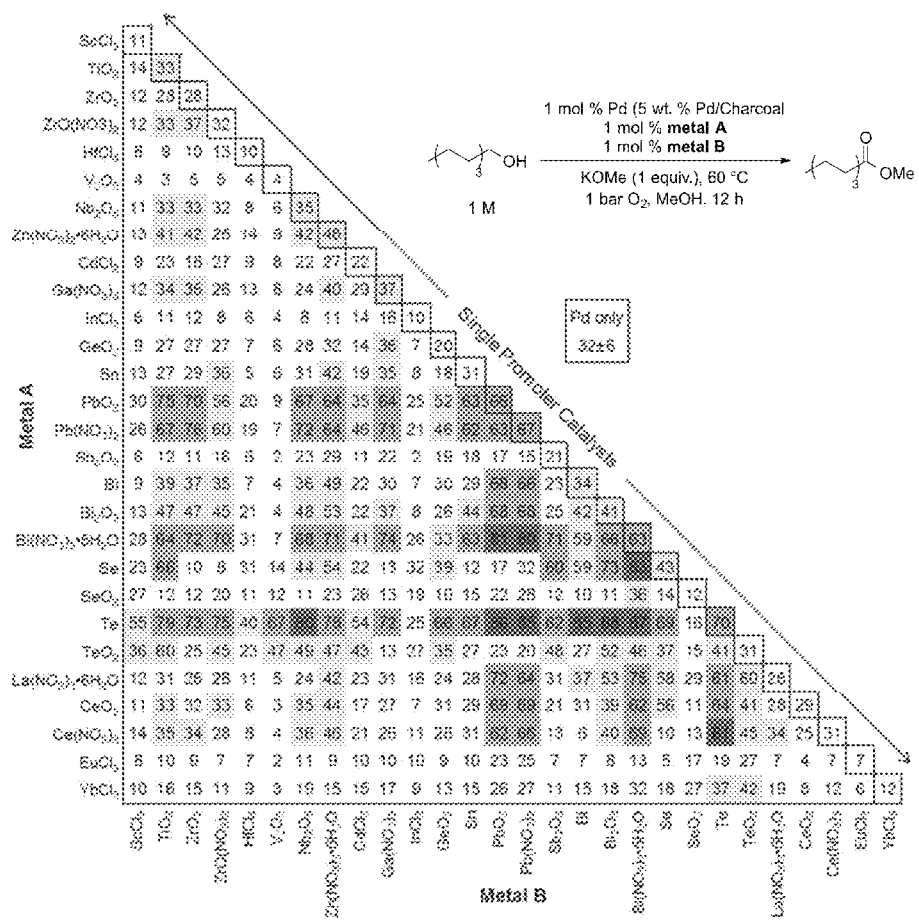
FIG. 11 shows admixture screening data (methyl octanoate yields) obtained from the aerobic oxidation of 1-octanol with heterogeneous catalysts composed of Pd/charcaol in combination with one or two additives. Shading reflects methyl octanoate yields: below that obtained with Pd alone (not shaded), above Pd alone (lightest shading), >60% (medium shading), and >80% (darkest shading).

In order to test the utility of admixture screening, we selected 28 different additives as possible promoters, consisting of main-group, transition-metal and rare-earth sources in elemental, oxide, or salt formulations. In several cases, different forms of an element were tested [e.g., Bi, $Bi(NO_3)_3.5H_2O$, and $Bi_2O_3$]. Pd/charcoal (5 wt. %) was combined with one or two of these components in a 1:1 or 1:1:1 molar ratio, respectively, and the diverse admixtures were tested as catalysts for aerobic oxidative methyl esterification of 1-octanol in methanol at 60° C. 1-Octanol was selected for testing because aliphatic alcohols tend to be significantly more difficult to oxidize relative to benzylic alcohols. Overall, 406 unique admixtures, with 231 different elemental combinations, were tested as catalysts for the reaction, and the results are depicted in FIG. 11.

Pd/charcoal itself shows modest activity for oxidation of 1-octanol under the reaction conditions, affording methyl octanoate in 32% yield, and the additives exhibit both poisoning and promoting effects on the catalyst, with yields ranging from 2-88%. The most effective single-component promoters observed in these studies (diagonal edge of FIG. 11) derive from sources of the main-group elements, Bi, Pb, and Te. Two-promoter combinations containing these elements exhibit even higher yields (medium and dark shading in FIG. 11). Some of the additives inhibit catalytic activity (e.g. $HfCl_4$ and $V_2O_5$), while a number of others have little or no effect on the reaction (e.g. Sn, $CeO_2$). Overall, the highest yields were observed when Bi- or Pb-based additives were combined with elemental Te as a second additive.

It is reasonable to expect that the "admixture screening" approach used here, like many other primary screening approaches, exhibits false-negatives. For example, the lack of effort to prepare specific catalyst formulations could miss active compositions among additives that are too insoluble to interact chemically with Pd in an admixture suspension. This limitation is offset, however, by the simplicity/accessibility of the method and, more importantly, by the number of successful "hits" observed from the method. Many component mixtures exhibit significantly enhanced activity relative to the Pd/charcoal benchmark. The successful admixtures represent convenient catalyst systems that may be use in laboratory-scale synthetic applications, but they also serve as important starting points for development of robust catalyst formulations that could be used in large-scale applications. As catalysts composed of Pd, Bi and Te were the most effective admixtures, these elements were selected to pursue the latter goal, as elaborated below.

Synthesis and Optimization of $PdBi_xTe_y/C$ Heterogeneous Catalysts.

Catalysts containing well-defined elemental compositions were prepared via wet-impregnation of Pd/C with Bi and Te precursors. $Bi(NO_3)_3.5H_2O$ and $TeCl_4$ were dissolved in an aqueous solution of dilute HCl and $HNO_3$ and added to a suspension of Pd/C in water. Excess formaldehyde (37 wt. % in water) was added to this mixture to reduce the promoters that had adsorbed to the Pd/C catalyst. The catalysts were then filtered, washed with excess water, and dried in a vacuum oven prior to use. ICP-AES analysis of the catalysts indicated that all of the Bi and Te used in the impregnation step were retained in the final catalyst, and SEM-EDX analysis showed that the promoters were predominantly co-localized with Pd on the carbon support.

PdBiTe catalysts prepared by this method were tested in the oxidative methyl esterification of 1-octanol with $K_2CO_3$ as the base,[19] and response surface methodology[20,21] was used to optimize the Bi and Te stoichiometry in the catalyst. A catalyst composed of a Pd:Bi:Te ratio of 1:1:1 was used as a starting point, and four surrounding compositions were used to determine the gradient associated with Bi and Te mole-fraction leading to improved activity (FIG. 12A). The path of steepest ascent was followed over four iterations to a catalyst consisting of $PdBi_{0.33}Te_{0.15}$, after which a number of compositions in this region were prepared to identify the best catalyst(s).[22] The results did not show a sharp peak for the optimal catalyst; rather, a relatively broad of range of catalyst compositions led to high yields of methyl octanoate (FIG. 12B). Two of the best catalyst compositions, $PdBi_{0.47}Te_{0.09}$ (PBT-1) and $PdBi_{0.35}Te_{0.23}$ (PBT-2) were carried forward for further investigation.

Reaction time-courses for the oxidative methyl esterification of 1-octanol were monitored to assess the activity of the PBT-1 and PBT-2 catalysts relative to the previously reported admixture catalyst, which consists of 1 mol % Pd/charcoal (5 wt %), 5 mol % $Bi(NO_3)_3.5H_2O$, 2.5 mol % Te. Catalysts incorporating only Bi or Te (in the mole-fractions associated with PBT-2), as well as Pd/C alone, were tested for comparison (FIG. 13). Pd/C shows negligible activity under the reaction conditions (FIG. 13, diamonds), while incorporation of Bi or Te leads to considerable improvement in performance (FIG. 13, circles and squares, respectively). Catalysts incorporating both Bi and Te, including PBT-1, PBT-2 and the admixture (FIG. 13, diamonds, triangles, and inverted triangles, respectively), show further improvement in activity over the single-promoter catalysts, with PBT-1 giving the best results. The synergy evident between Bi and Te was confirmed by showing that simply increasing the quantity of Bi or Te in single-promoter catalyst did not improve the catalyst performance (see Table 2).

TABLE 2

Yield of methyl octanoate with single promoter catalysts.[a]

| catalyst | yield (%) |
|---|---|
| $PdBi_{0.05}$ | 8 |
| $PdBi_{0.5}$ | 0 |
| $PdBi_5$ | 3 |
| $PdTe_{0.23}$ | 0 |
| $PdTe_{0.43}$ | 6 |
| $PdTe_{0.67}$ | 2 |

[a]1M 1-octanol, 1 eq. KOMe, 1 bar O2, 24 h, 60° C., MeOH solvent, 1 mol % Pd.

Batch Reaction Data with PdBiTe Catalysts.

The previously reported PdBiTe admixture catalyst tolerates a wide range of functional groups,[17] and in order to compare the performance of the newly formulated PBT-1 catalyst, ten representative primary alcohols, including those with heterocycles and halide-containing functional groups, were tested in batch reactions at 1 mol % Pd loading (Scheme 1). Each of the primary alcohol substrates underwent oxidation to the corresponding methyl ester in >90% yield within 8 h. Benzylic alcohols are considerably more reactive than aliphatic alcohols, and benzyl alcohol 1a afforded the methyl ester in near-quantitative yield (>99%) in 2 h with only 0.1 mol % PBT-1. The data show that PBT-1 exhibits scope closely resembling the admixture catalyst, while improving the product yields (up to 16%) and reactions rates (approx. two-fold) under comparable conditions for a number of the alcohols.

Figure 14A:
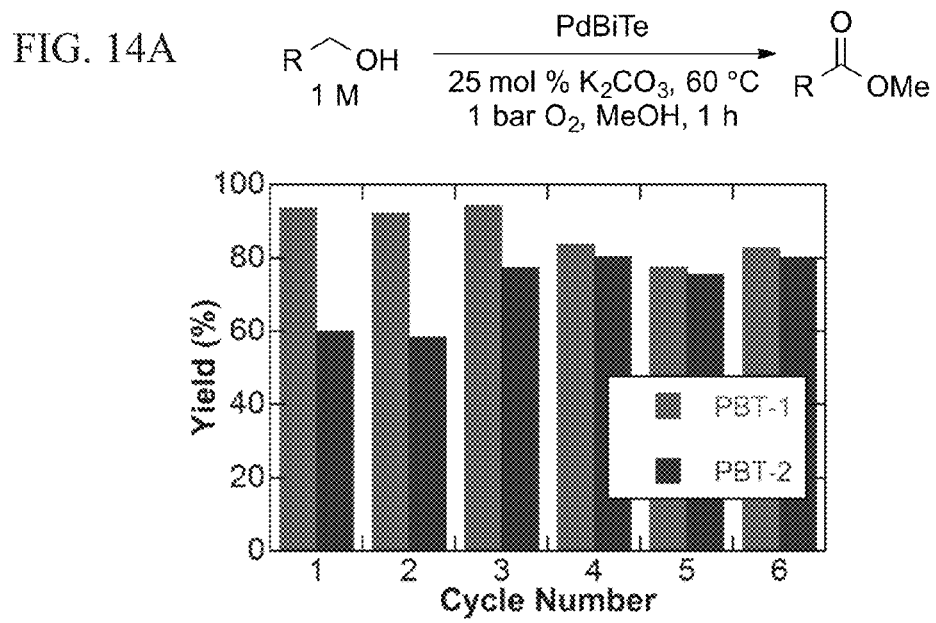
FIGS. 14A and 14B show batch recycling of PBT-1 and PBT-2 Catalysts in the oxidative methyl esterification of benzyl alcohol (FIG. 14A) and 1-octanol (FIG. 14B). Catalyst loading: 0.1 mol % Pd for benzyl alcohol; 1 mol % Pd for 1-octanol.
Figure 14B:
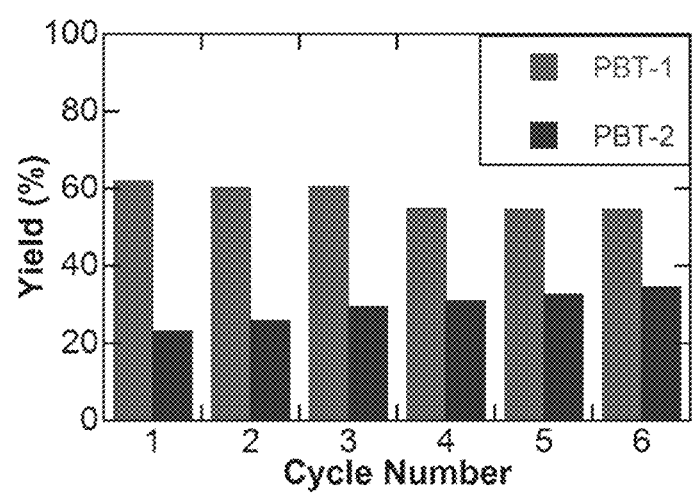
Figure 15:
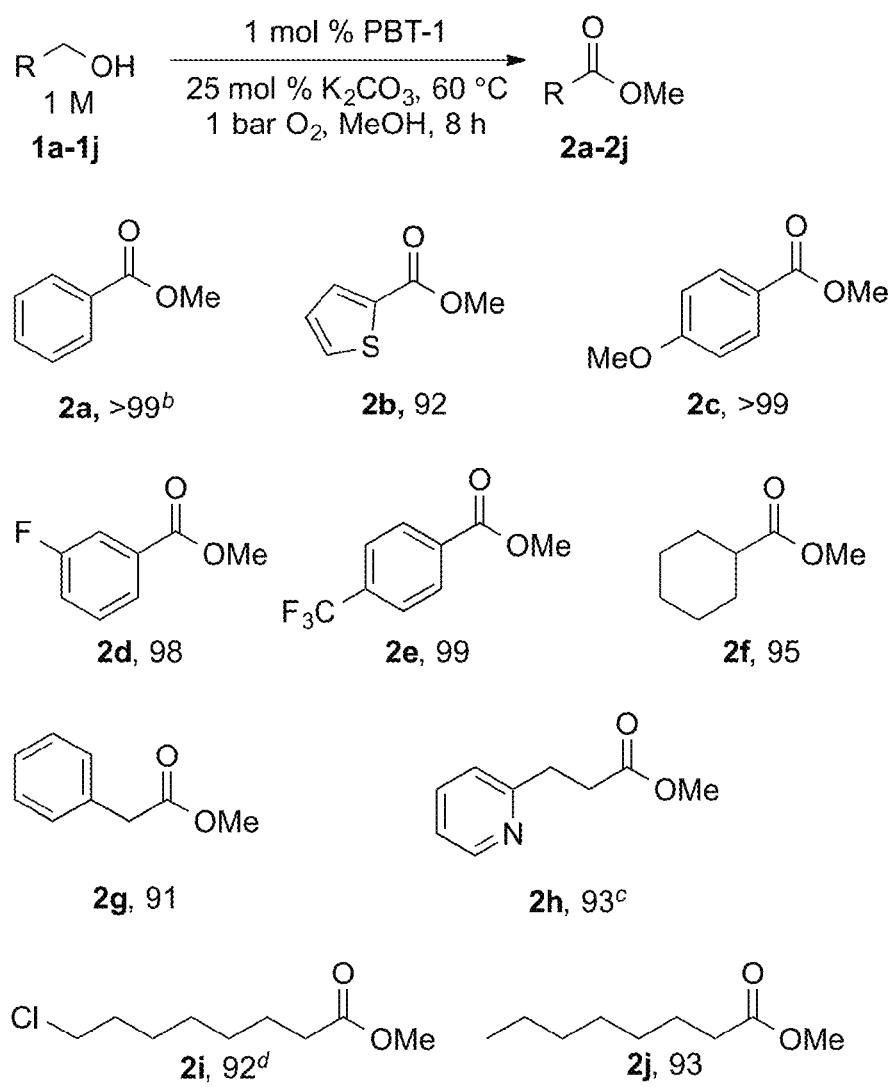
FIG. 15 is a schematic diagram showing the Scope of Aerobic Alcohol Esterification System with PBT-1. Reactions carried out on 1 mmol scale; $^1$H NMR yields with trimethoxybenzene as internal standard. $^b$0.1 mol % Pd, 2 h. $^c$2 mol % Pd. $^d$5 mol % Pd.

Both PBT-1 and PBT-2 retained good activity upon recycling in the oxidation of benzyl alcohol and 1-octanol (FIGS. 14A and 14B). The reactions were stopped at incomplete conversion in order to increase the sensitivity of the tests to changes in catalyst activity. PBT-1 showed a small decrease in yield for cycles 4-6 relative to cycles 1-3, but otherwise showed steady performance. PBT-2 exhibited modest improvement in performance during the recycle tests. Possible complications associated with these types of experiments (e.g., mechanical losses in catalyst recovery) make us hesitant to draw definitive conclusions from the small changes, however, and in order to carry out a more rigorous assessment of the catalyst stability, we investigated the performance of PBT-1 and PBT-2 under continuous process conditions.

Continuous Process Data with PdBiTe Catalysts.

Figure 16:
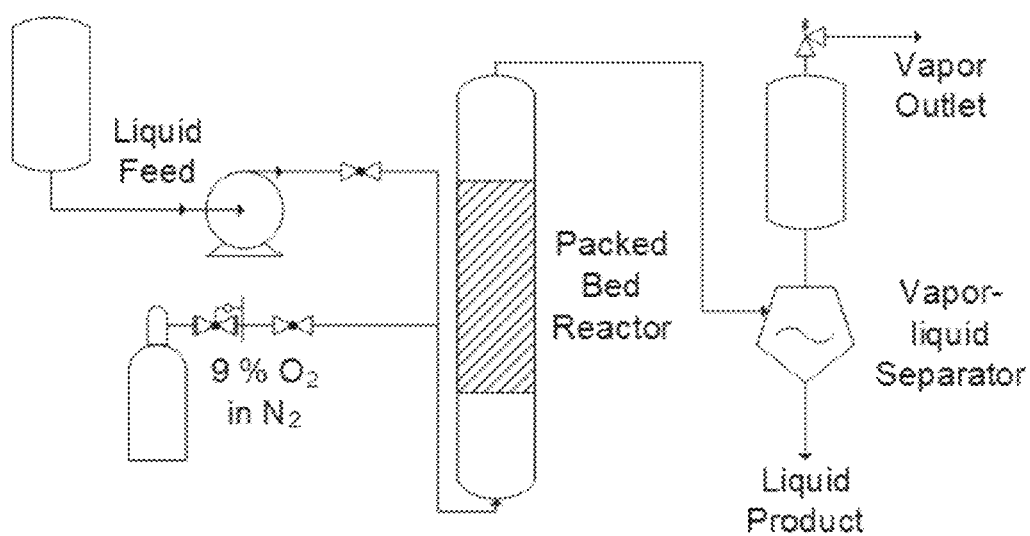
FIG. 16 is a schematic diagram of the flow reactor.

The performance of the PdBiTe catalysts under continuous process conditions was assessed by incorporating the catalyst into a packed-bed reactor (FIG. 16).[i] A solution of the primary alcohol was mixed with a diluted $O_2/N_2$ gas stream at a tee, and the gas-liquid mixture was fed into a packed bed reactor containing the catalyst. After exiting the reactor, the gas and liquids were separated and the product was collected. The progress of the reaction was monitored by taking aliquots from a sample collection port and performing GC analysis.

Initial testing of 1-octanol oxidation with the PdBiTe catalysts revealed a complication that was not evident from the batch reactions. The yield of methyl octanoate reached a plateau at ~80%, and no improvement was realized by varying the liquid and gas flow rates, $O_2$ pressure, and 1-octanol concentration. These results prompted us to search for potential catalyst poisons. Octyl aldehyde (3) is an expected intermediate in the esterification reaction, and when it was tested as a substrate, the reaction led to complete conversion of the aldehyde but only ~50% selectivity for methyl octanoate. Aldol condensation products 4 and 5 were identified as by-products and accounted for the remaining mass balance (eq 1). Subsequent studies showed that these aldol products strongly inhibit oxidation of 1-octanol.[24]

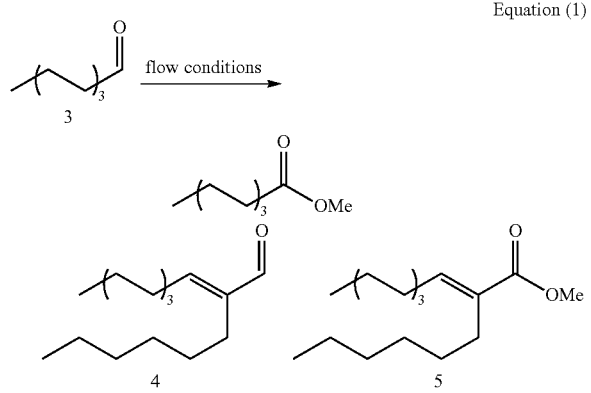

Equation (1)

While both alcohol oxidation and aldol condensation are promoted by Brønsted bases, we speculated that the aldol reaction could be minimized by using a lower concentration of $K_2CO_3$. This hypothesis was validated, as shown in Table 3, by using a four-fold lower $K_2CO_3$ concentration. Under these conditions, an excellent yield of methyl octanoate (96%) could be obtained.[25]

TABLE 3

Optimization of Flow Conditions to Achieve High Steady-State Yields in the Aerobic Oxidation of 1-Octanol.

| Entry | [$K_2CO_3$] (mM) | WHSV[a] (h$^{-1}$) | Yield (%)[b] |
|---|---|---|---|
| 1 | 62.5 | 10.6 | 79 |
| 2 | 31.3 | 10.6 | 82 |
| 3 | 15.6 | 10.6 | 72 |
| 4 | 15.6 | 2.66 | 96 |

[a]Weight hourly space velocity = mg alcohol/(mg Pd · hr).
[b]Determined by GC vs an internal standard.

Figure 17:
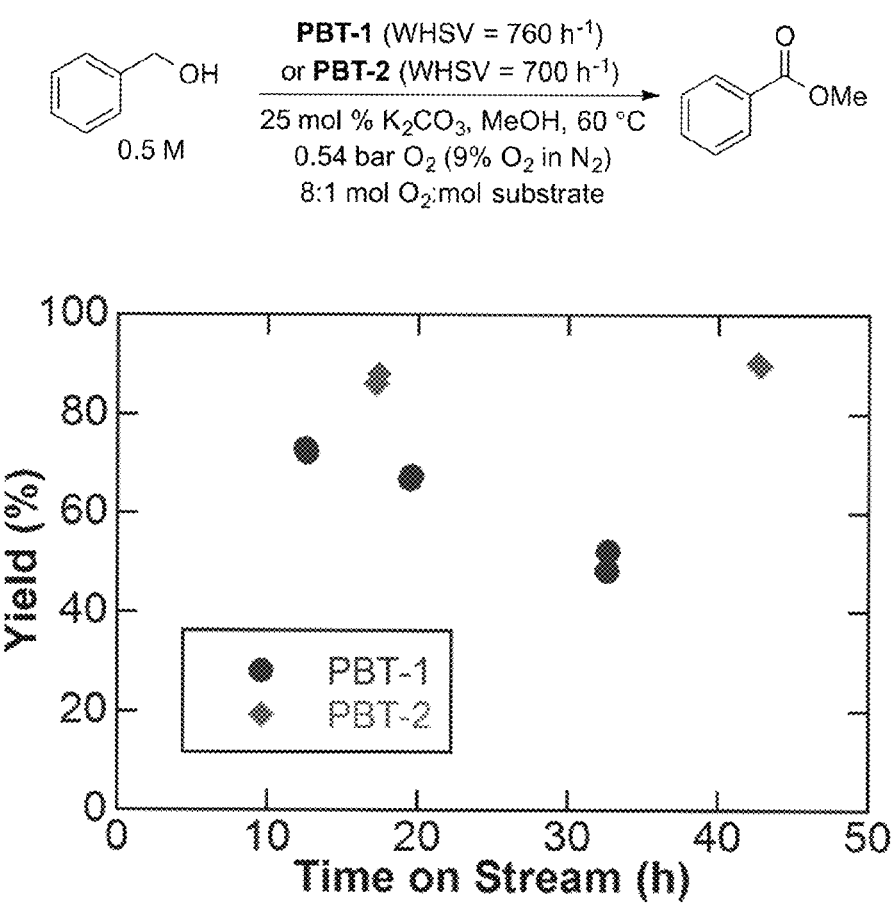
FIG. 17 shows long-term testing of PBT-1 and PBT-2 catalysts under continuous conditions for the oxidative methyl esterification of benzyl alcohol.

As observed under batch reaction conditions, the PdBiTe catalysts exhibit much higher activity for the oxidation of benzyl alcohol to methyl benzoate than for the oxidation of 1-octanol. These faster rates facilitated testing of the catalyst performance during extended use. Long-term assessment of the PBT-1 catalyst for benzyl alcohol oxidation revealed a steady decrease in catalyst activity during a 33 h test at a WHSV of 760 h$^{-1}$ (FIG. 17, circles). In contrast, the PBT-2 catalyst showed excellent long-term stability over 43 h at a WHSV of 700 h$^{-1}$ (FIG. 17, diamonds). Further testing was therefore carried out with PBT-2, and a scan of different flow rates showed that methyl benzoate reached near quantitative yields at a WHSV of 500 h$^{-1}$ (FIG. 18A). With these conditions, no decrease in the product yield was observed after nearly 60,000 catalytic turnovers (FIG. 18B).

Figure 19A:
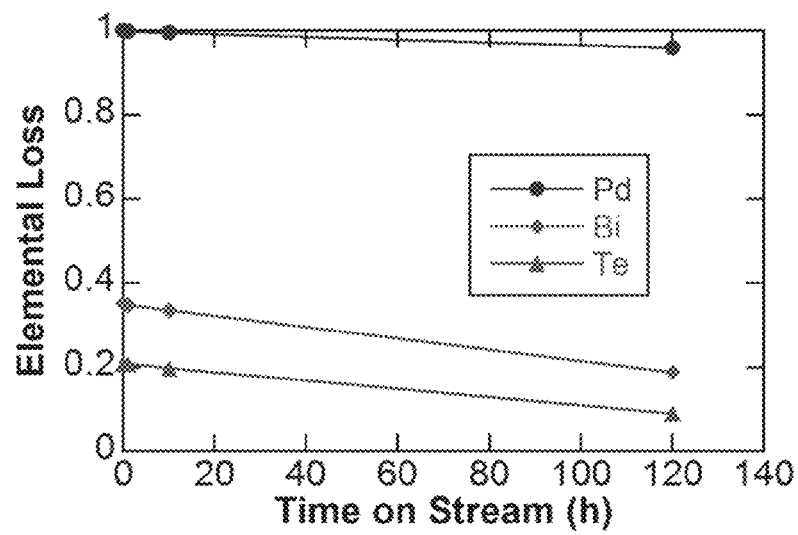
FIGS. 19A and 19B show elemental leaching studies.
Figure 19B:
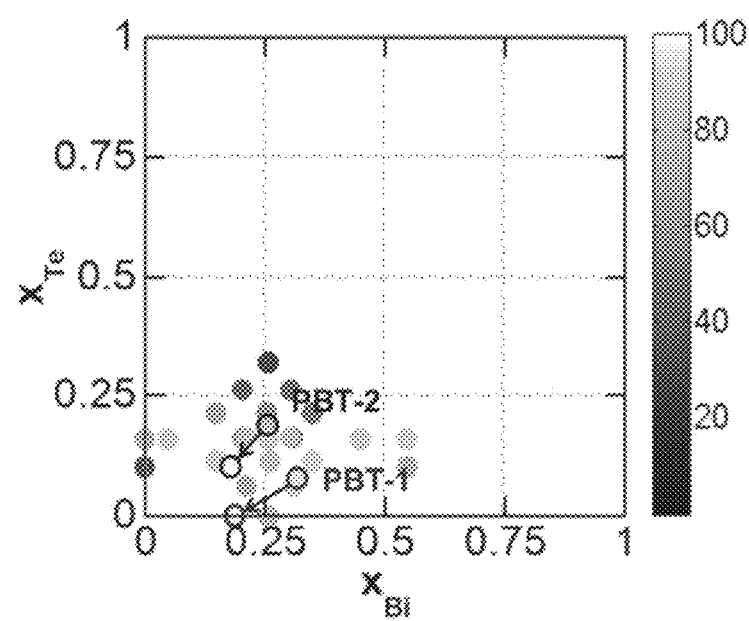

The reactor effluent from the extended run with the PBT-2 catalyst was analyzed by ICP-AES to determine the extent of leaching of the different catalyst components: Pd, Bi, and Te (Table 4), and the final product solution contained less than one part-per-million of the three elements: 0.025, 0.20, and 0.10 ppm of Pd, Bi and Te, respectively. Even with this low level of leaching, the high turnover numbers led to modest changes in the catalyst composition during the course of the reaction (FIG. 19A). During the experiment shown in FIG. 18B, the leaching resulted in a change of the PBT-2 catalyst from a stoichiometry of $PdBi_{0.35}Te_{0.21}$ to $PdBi_{0.21}Te_{0.12}$, on the basis of ICP-AES analysis of the catalyst before and after the reaction (FIG. 19B, dark circles). A similar analysis of the PBT-1 catalyst used in the long-term flow run revealed no detectable levels of Te remaining the catalyst after the reaction (FIG. 19B, light circles). These observations account for the different performance of PBT-1 and PBT-2 during continuous operation. PBT-2 starts with higher mole-fraction of Te, and the catalyst composition remains in the region of high activity, despite partial leaching, whereas a similar leaching rate with PBT-1 results in complete depletion of the Te component.

TABLE 4

Average effluent concentrations of Pd, Bi, and Te between 0-1, 1-10, and 10-120 h, and the corresponding mass of Pd, Bi, and Te lost from original catalyst.

| Element | Time on Stream (h) | Effluent Concentration (ppb) | % Lost from Initial Catalyst |
|---|---|---|---|
| Pd | 0-1 | 140 | 0.19 |
| | 1-10 | 15 | 0.19 |
| | 10-120 | 25 | 3.7 |
| Bi | 0-1 | 200 | 0.39 |
| | 1-10 | 200 | 3.6 |
| | 10-120 | 200 | 42 |
| Te | 0-1 | 110 | 0.60 |
| | 1-10 | 110 | 5.3 |
| | 10-120 | 88 | 51 |

Analysis of the reaction rate at different temperatures (50-80° C.) under flow conditions provided the basis for Arrhenius analysis of PBT-2-catalyzed oxidation of benzyl alcohol (FIG. 20), which revealed that the reaction exhibits an activation energy of 87 kJ/mol and a pre-exponential of $6 \times 10^{12}$ s$^{-1}$. These values correspond to a turnover frequency of 540 h$^{-1}$ at the reaction temperature of 60° C. typically used in our study. The large pre-expontential term is consistent with a surface-mediated rate-limiting step involving bound substrate.[26] More thorough mechanistic studies are the focus of ongoing work, but the Arrhenius parameters may be compared to data obtained with a AuPd/TiO$_2$ catalyst, which is one of the most active known heterogeneous catalysts for alcohol oxidation.[27] The activation energy for the oxidation of benzyl alcohol with the AuPd/TiO$_2$ catalyst is 56 kJ/mol and has a pre-exponential of 1.5×10$^8$ s$^{-1}$. The AuPd catalyst was only investigated at elevated temperatures (100-160° C.); however, at a benchmark temperature of 100° C. for both catalysts, the calculated TOFs correspond to 15,500 h$^{-1}$ for PdBiTe (PBT-2) and 8000 h$^{-1}$ for AuPd (TOF values reflect the rate on a per Pd and Au+Pd atom basis, respectively).

Conclusion

In summary, this example demonstrates a promising new approach for the discovery of novel heterogeneous catalysts. New Pd-based catalyst compositions were identified via the screening of simple admixtures of commercially available components, including Pd/charcoal and various possible promoters in their elemental, oxide, or salt formulations. The screening data revealed a number of highly promising compositions that provided a foundation for subsequent development and optimization of more-precise heterogeneous catalyst formulations. These efforts led to two highly effective PdBiTe catalysts that show excellent activity for the oxidative methyl esterification of diverse primary alcohols. One of these, with a composition of PdBi$_{0.35}$Te$_{0.21}$/C (PBT-2), was shown to have excellent good stability and excellent performance under continuous flow conditions in a packed-bed reactor, and it represents the most active liquid-phase oxidative esterification catalyst reported to date.

Methods

General Considerations.

Commercially available reagents and solvent were obtained from commercial sources and used as received. No precautions were taken to exclude air or water from the solvent or reaction mixtures. $^1$H NMR spectra were recorded on a Varian MercuryPlus 300 MHz spectrometer. SEM-EDX particle images and elemental analyses were performed using a LEO SUPRA 55 VP scanning electron microscope (SEM) coupled with a Thermo-Fischer Noran System 7 energy dispersive X-ray spectroscopy (EDX) detector.

Catalyst Preparation.

500 mg of 5 wt. % Pd/C[28] was mixed with 15 mL of DI water. Bi(NO$_3$)$_3$.5H$_2$O and [TeCl$_4$]$_4$ were dissolved in a mixture of 1 M HCl (1 mL) and conc. HNO$_3$ (0.1 mL) and added to the catalyst suspension. The Pd/C and dissolved Bi and Te salts were mixed at 50° C. for 3 h. After 3 h, 500 mL of a 30% NaOH solution was added to make the mixture alkaline. 200 mL of 37% formaldehyde was then added and the mixture was heated to 80° C. under N$_2$ for 16 h. The catalyst was then filtered and washed with water (~500 mL) until neutral. The catalyst was then dried under vacuum at 70° C. for 20 hours to afford the final catalyst.

GC Method and Retention Times.

GC analyses were performed using a DB-Wax column (Length=30 m, i.d.=0.25 mm) installed in a Shimadzu GC-17A equipped with a flame-ionization detector. An 11 min GC method was used consisting of a 1 min hold at 70° C., ramp at 20° C./min from 70° C. to 200° C. (6.5 min), and a 3.5 min hold at 200° C. The injector and detector were held at 225° C. and the column flow was 1.5 mL/min of He with a split ratio of 20. Retention times were as follows: benzyl alcohol (7.7 min), benzaldehyde (5.7 min), methyl benzoate (6.3 min), 1-octanol (5.7 min), octyl aldehyde (4.0 min), methyl octanoate (4.7 min), and mesitylene (3.7 min).

Procedure for the Batch Reaction Oxidation of Alcohols.

MeOH (0.5 mL) was added to 20×150 mm culture tube containing 21.3 mg of PBT-2 (1 mol % Pd) and 34.6 mg K$_2$CO$_3$ (25 mol %) and was then placed on an orbital shaker and agitated under 1 atm O$_2$ for 30 min while heating to 60° C. Once the reaction temperature was reached, the headspace was purged with O$_2$, and the substrate was added as a 2 M solution in MeOH (0.5 mL) containing 0.2 M mesitylene as an internal standard (I. S.). The post reaction solution was injected onto a GC to determine product and reactant concentrations. The catalyst was recovered by filtration or centrifugation.

Procedure for the Batch Recycling of the Catalyst.

Upon completion of a reaction cycle, the test tube containing the reaction mixture was centrifuged at 1000 rpm for 5 min. The supernatant was decanted and the solid material was rinsed with fresh MeOH by resuspending the catalyst, centrifuging the mixture at 1000 rpm for 5 min, followed by decanting the supernatant. Fresh K$_2$CO$_3$ was added and a new reaction was performed by using the procedure for the batch reaction oxidation of alcohols described above.

Preparation of the Packed-Bed Reactor.

The packed bed reactor was made from a stainless steel tube 0.25" o.d.×3" with 1 cm of glass wool inside a Swagelok fitting with a 200 mesh stainless steel screen. Powdered catalyst (0.4 g PBT-2) was added, leaving 1 cm of open space for more glass wool to be retained by another 200 mesh stainless steel screen and a Swagelok fitting.

Procedure for Alcohol Oxidation under Flow Conditions.

A solution of 5 M benzyl alcohol and 1 M mesitylene in MeOH was added to a 260 mL syringe pump (Teledyne ISCO 260D), and 0.138 M K$_2$CO$_3$ in MeOH was added to a second 260 mL syringe pump. The flow rate of the second pump was set to 9 times that of the pump containing alcohol to afford a final liquid solution of 0.5 M benzyl alcohol, 0.1 M mesitylene, and 0.125 M K$_2$CO$_3$ in MeOH. A cylinder of 9% O$_2$ in N$_2$ was regulated down to 15 bar and the gas flow rate was controlled by a mass flow controller with a O$_2$ to substrate molar ratio of 8:1. The gas and liquids were mixed in two ⅛" tees and sent through a heated zone, after which they passed through the packed bed reactor (PBR) in an up-flow configuration. The preheated zone and packed-bed reactor were submerged in ethylene glycol heat transfer fluid maintained at 60° C. The weight hourly space velocity (WHSV) was controlled by adjusting the gas and liquid flow rates to the appropriate level. Aliquots of the reaction mixture (100-500 mL) could be removed through a small tee for GC analysis, and the remaining liquid and gas were separated using a large tee with the liquids collected out the bottom using a level gauge and the gases vented out the top through a pressure relief valve. The pressure relief valve controls the reaction pressure and was maintained at 6 bar.

ICP-AES Analysis of the Catalyst.

The catalyst (25 mg PBT-2) was added to a crucible and heated at 450° C./min to 900° C. and held at this temperature for 2 hours. After cooling, the crucible was filled with aqua regia and heated on a hot plate to the boiling point. After 3 hours, the aqua regia was collected in a 100 mL volumetric flask and diluted up to 100 mL using 9% HCl. The solution was analyzed on a Perkin Elmer Instruments Optima 2000 DV ICP AES.

Supporting Information
Response-Surface Methodology Data for PdBiTe Catalyst Optimization.

General reaction conditions for the oxidative methyl esterification of 1-octanol by PdBiTe catalysts.

Scheme 2:

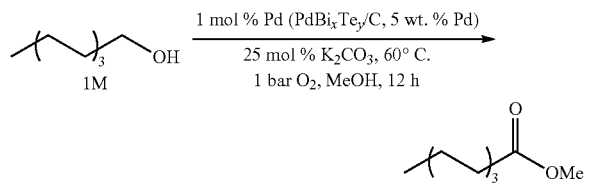

In the development of catalysts with defined catalyst compositions, paths of steepest ascent were followed from a starting point of $Pd_1Bi_1Te_1/C$ towards an optimum catalyst. Data were obtained from two independent efforts (Paths A and B). All experiments were performed under the conditions in Scheme 2. Path A was carried out by taking constant step sizes of 0.1 unit, and path B was carried out by taking larger step sizes of approximately half the distance to an axis. Similar paths were taken for both with the path of steepest ascent first decreasing $x_{Bi}$ of approx. 0.3, then decreasing $x_{Te}$ to approx. 0.15. Both paths ended at a region of high activity from which $PdBi_{0.35}Te_{0.23}/C$ (PBT-2) and $PdBi_{0.47}Te_{0.09}/C$ (PBT-1) were chosen.

Catalyst Stability in Batch and Flow.

To assess the activity and long-term stability of the two PBT catalysts, a continuous flow run was performed at different WHSV's and over an extended reaction time at a constant WHSV (Figure S6A and B). The PBT-2 catalyst has higher activity for the oxidation of benzyl alcohol in the flow reactor with quantitative yields obtained at a WHSV of 500 h$^{-1}$ (1/WHSV=7.2 s). The catalyst stability was measured by holding the reactor at a constant elevated WHSV of 700 h$^{-1}$ (1/WHSV~5 s), and the product yield was monitored over an extended time period. After 33 h and 22,000 turnovers, the yield of methyl benzoate produced from the reaction with PBT-1 decreased from 73 to 50%. In contrast, the reaction with PBT-2 showed no loss in activity after 43 h and 27,000 turnovers. Therefore, PBT-2 was chosen for the demonstration of a 5 day continuous process.

Origin of Catalyst Poisoning by 1-Octanol in the Flow Reactor.

Catalyst poisoning under flow reaction conditions was manifested as a limit to the maximum attainable conversion of 1-octanol. Recycling of reactor effluent back through the reactor showed no increase in concentration of methyl octanoate. In addition, spiking the feed solution with methyl octanoate or octanoic acid yielded 80% conversion of 1-octanol to methyl octanoate, showing that neither of these species poisons the catalyst. In contrast, use of octyl aldehyde as the starting material afforded only 50% yield of methyl octanoate at 100% conversion of octyl aldehyde. A fresh sample of 1-octanol was added to the reactor effluent and the mixture was re-fed through the reactor under standard reaction conditions. This run afforded only 7.5% conversion of the alcohol, indicating that a catalyst poison is generated during the oxidation of octyl aldehyde. The missing mass from the initial reaction of octyl aldehyde was identified as 2-hexyl-2-decenal and methyl 2-hexyl-2-decenoate by GC-MS, $^1$H NMR, and $^{13}$C NMR, reflecting aldol self-condensation of octyl aldehyde.

Example 1 References Cited (1) Sheldon, R. A.; Bekkum, H. v., *Fine Chemicals through Heterogeneous Catalysis*, 2007, DOI: 10.1002/9783527612963
(2) Twigg, M. V., *Catalyst Handbook*, 2$^{nd}$ ed.; Wolfe Publishing Ltd: Frome, 1989.
(3) (a) Lindlar, H. *Helv. Chim. Acta* 1952, 35, 446. (b) Lindlar, H.; Dubuis, R. Org. Synth. 1966, 46, 89.
(4) (a) Stiles, A. B., Catalyst Manufacture: Laboratory and Commercial Preparation. In *Chemical Industries*; Marcel Dekker, Inc: New York, 1983; Vol. 14. (b) Farrauto, R. J.; Bartholomew, C. H., *Fundamentals of Industrial Catalytic Processes*, Chapman & Hall: Ney York, 1997.
(5) Hagemeyer, A.; Volpe, A. F., *Modern Applications of High Throughput R&D in Heterogeneous Catalysis*, 2014, DOI: 10.2174/97816080587231140101.
(6) For representative primary references, see: (a) Liu, Y.; Cong, P.; Doolen, R. D.; Guan, S.; Markov, V.; Woo, L.; Zeyβ, S.; Dingerdissen, U., *Appl. Catal. A Gen.*, 2003, 254, 59-66. (b) Guram, A.; Hagemeyer, A.; Lugmair, C. G.; Turner, H. W.; Volpe Jr, A. F.; Weinberg, W. H.; Yaccato, K., *Adv. Synth. Catal.*, 2004, 346, 215-230. (c) Yamada, Y.; Kobayashi, T., *J. Jpn. Petrol. Inst.*, 2006, 49, 157-167.
(7) For reviews, see: (a) Besson, M.; Gallezot, P., *Catal. Today*, 2000, 57, 127-141. (b) Mallat, T.; Baiker, A., *Appl. Catal. A: Gen.*, 2000, 200, 3-22. (c) Mallat, T.; Baiker, A. *Chem. Rev.* 2004, 104, 3037-3058. (d) Vinod, C. P.; Wilson, K.; Lee, A. F., *J. Chem. Technol. Biotechnol.*, 2011, 86, 161-171.
(8) For representative primary references, see: (a) Angerstein-Kozlowska, H.; MacDougall, B.; Conway, B. E., *J. Electrochem. Soc.*, 1973, 120, 756-766. (b) Aoshima, A.; Suzuki, Y.; Yamamatsu, S.; Yamaguchi, T., U.S. Pat. No. 4,518,796, May 21, 1985. (c) Smits, P. C. C.; Kuster, B. F. M.; Wiele, K. v. d.; Baan, H. S. v. d., *Appl. Catal.*, 1987, 33, 83-96. (d) Tsujino, T.; Ohigashi, S.; Sugiyama, S.; Kawashiro, K.; Hayashi, H. *J. Mol. Catal.* 1992, 71, 25-35. (e) Kimura, H.; Kimura, A.; Kokubo, I.; Wakisaka, T.; Mitsuda, Y., *Appl. Catal. A: Gen.*, 1993, 95, 143-169. (f) Besson, M.; Lahmer, F.; Gallezot, P.; Fuertes, P.; Flèche, G., *J. Catal.*, 1995, 152, 116-121. (g) Wenkin, M.; Touillaux, R.; Ruiz, P.; Delmon, B.; Devillers, M., *Appl. Catal. A: Gen.*, 1996, 148, 181-199. (h) P. Fordham, P.; Besson, M.; Gallezot, P., *Catal. Lett.*, 1997, 46, 195-199. (i) Wenkin, M.; Ruiz, P.; Delmon, B.; Devillers, M., *J. Mol. Catal. A. Chem.*, 2002, 180, 141-159. (j) Anderson, R.; Griffin, K.; Johnston, P.; Alsters, P. L. *Adv. Synth. Catal.* 2003, 345, 517-523. (k) Keresszegi, C.; Mallat, T.; Grunwaldt, J.-D.; Baiker, A., *J. Catal.*, 2004, 225, 138-146. (l) Mondelli, C.; Ferri, D.; Grunwaldt, J.-D.; Krumeich, F.; Mangold, S.; Psaro, R.; Baiker, A., *J. Catal.*, 2007, 252, 77-87. (m) Mondelli, C.; Grunwaldt, J.-D.; Ferri, D.; Baiker, A., *Phys. Chem. Chem. Phys.*, 2010, 12, 5307-5316. (n) Fan, A.; Jaenicke, S.; Chuah, G.-K., *Org. Biomol. Chem.*, 2011, 9, 7720-7726. (o) Frassoldati, A.; Pinel, C.; Besson, M. *Catal. Today* 2011, 173, 81-88. (p) Witońska, I.; Frajtak, M.; Karski, S. *Appl. Catal. A: Gen.*, 2011, 401, 73-82. (q) Bowman, R. K.; Brown, A. D.; Cobb, J. H.; Eaddy, J. F.; Hatcher, M. A.; Leivers, M. R.; Miller, J. F.; Mitchell, M. B.; Patterson, D. E.; Toczko, M. A.; Xie, S. *J. Org. Chem.* 2013, 78, 11680-11690.

(9) For leading references, see: (a) Steinhoff, B. A.; Guzei, I. A.; Stahl S. S. *J. Am. Chem. Soc.*, 2004, 126, 11268-11278. (b) Steinhoff, B. A.; Stahl, S. S. *J. Am. Chem. Soc.*, 2006, 128, 4348-4355. (c) Ye, X.; Johnson, M. D.; Diao, T.; Yates, M. H.; Stahl, S. S. *Green Chem.*, 2010, 12, 1180-1186.

(10) For reviews, see: (a) Sheldon, R. A.; Arends, I. W. C. E.; Brink, G.-J., T.; Dijksman, A. *Acc. Chem. Res.* 2002, 35, 774-781. (b) Zhan, B.-Z.; Thompson, A. *Tetrahedron* 2004, 60, 2917-2935. (c) Stahl, S. S. *Angew. Chem. Int. Ed.* 2004, 43, 3400-3420. (d) Schultz, M. J.; Sigman, M. S. *Tetrahedron* 2006, 62, 8227-8241. (e) Parmeggiani, C.; Cardona, F. *Green Chem.* 2012, 14, 547-564.

(11) Precedents for the oxidative esterification of benzylic alcohols were reported recently: (a) Gowrisankar, S.; Neumann, H.; Beller, M. *Angew. Chem., Int. Ed.* 2011, 50, 5139-5143. (b) Liu, C.; Wang, J.; Meng, L.; Deng, Y.; Li, Y.; Lei, A. *Angew. Chem., Int. Ed.*, 2011, 50, 5144-5148.

(12) Rodriguez-Reyes, J. C. F.; Siler, C. G. F.; Liu, W.; Tkatchenko, A.; Friend, C. M.; Madix, R. J., *J. Am. Chem. Soc.*, 2014, 136, 13333-13340.

(13) Salam, N.; Banerjee, B.; Roy, A. S.; Mondal, P.; Roy, S.; Bhaumik, A.; Islam, S. M., *Appl. Catal. A: Gen.*, 2014, 477, 184-194.

(14) Su, F.-Z.; Ni, J.; Sun, H.; Cao, Y.; He, H.-Y.; Fan, K.-N., *Chem. Eur. J.*, 2008, 14, 7131-7135.

(15) Kaizuka, K.; Miyamura, H.; Kobayashi, S., *J. Am. Chem. Soc.*, 2010, 132, 15096-15098.

(16) Jagadeesh, R. V.; Junge, H.; Pohl, M.-M.; Radnik, J.; Brückner, A.; Beller, M., *J. Am. Chem. Soc.*, 2013, 135, 10776-10782.

(17) Powell, A. B.; Stahl, S. S. *Org. Lett.* 2013, 15, 5072-5075.

(18) $Bi(NO_3)_3 \cdot 5H_2O$ has been observed to activate heterogeneous Pd and Pt catalysts in the oxidation of 2-phenoxyethanols to the corresponding carboxylic acids: Fiege H.; Wedemeyer K., *Angew. Chem. Int. Ed.*, 1981, 20, 783-784.

(19) KOMe and $K_2CO_3$ have been shown previously to work nearly equally well with admixture catalysts (see ref 17) and the PBT-2 catalyst. Separate studies also showed that the effect of the base is not dependent on the alkali-metal counter ion; potassium salts were chosen for their availability and ease of use.

(20) (a) Box G. E. P. and Wilson K. B., *J. R. Stat. Soc.: Ser. B*, 1951, 13, 1-45. (b) Myers R.; Montgomery D., *Response surface methodology: process and product optimization using designed experiments*; Wiley: New York, 1995.

(21) For a recent example of RSM applied to chemistry see: Garcia-Cabeza, A. L.; Ray, L. P.; Marin-Barrios, R; Ortega, M. J.; Moreno-Dorado, F. J.; Guerra, F. M.; Massanet, G. M. *Org. Process Res. Dev.* 2014, DOI: 10.1021/op5002462.

(22) See Supporting Information below for additional catalyst optimization data.

(23) For more-thorough description of the reactor, see: Mannel D. S.; Stahl S. S.; Root T. W., *Org. Process Res. Dev.*, 2014, 18, 1503-1508.

(24) For previous observation of aldol products as catalyst poisons, see: Mallat, T.; Baiker, A., *Appl. Catal. A: Gen.*, 1992, 86, 147-163.

(25) See Supporting Information below for a discussion of aldol condensation product poisoning.

(26) Baetzold, R. C.; Somorjai, G. A., *J. Catal.*, 1976, 45, 94-105.

(27) Enache, D. I.; Edwards, J. K.; Landon, P.; Solsona-Espriu, B.; Carley, A. F.; Herzing, A. A.; Watanabe, M.; Kiely, C. J.; Knight, D. W.; Hutchings, G. J., *Science*, 2006, 311, 362-365.

(29) Pd/C was obtained from Sigma Aldrich (Aldrich number 276707) and used as received.

Example 2: Development of a Pd—Bi—Te/C Catalyst (PBT) for Aerobic Oxidation of Alcohols to Carboxylic Acids In this example, we provide more details regarding the aerobic oxidation of primary alcohols to the carboxylic acid that has been achieved with a heterogeneous Pd catalyst promoted by Bi and Te. The addition of Bi and Te accelerates the reaction rate and increases selectivity and yield for a variety of benzylic and aliphatic carboxylic acids with diverse functional groups. Catalyst stability is demonstrated with approximately 60,000 turnovers over a 2 day continuous run in a packed bed reactor with 99% yield of benzoic acid maintained throughout. Biomass derived 5-(hydroxymethyl)furfural (HMF) is also oxidized to the di-acid with yields of 95%. These results provide the basis for the selective aerobic oxidation of alcohols to carboxylic acids using a robust heterogeneous PdBiTe catalyst.

Introduction

The past two decades have seen a significant increase in the push for heterogeneous catalysts capable of sustainable, selective aerobic oxidations.[1] This is especially true within the fine and specialty chemical industries, which traditionally favor the employment of more classical methods, e.g. TEMPO/bleach,[2] potassium permanganate ($KMnO_4$),[3] and Jones reagent ($CrO_3/H_2SO_4$)[4] for the oxidation of alcohols to carboxylic acids. Traditional stoichiometric methods display exceptional functional group tolerance; however, increased concerns over environmental impacts; formation of inorganic salts, dangers associated with quenching large reactions, and limited scalability of reaction conditions, has limited the scalability of these methods.

Within organic synthesis, heterogeneous catalysts are most often associated with the reduction of various functional groups. For example Lindlar's catalyst ($Pd/CaCO_3$ doped with $Pb(OAc)_2$ and quinolone) has been shown to selectivity hydrogenate alkynes, to exclusively affords the alkene.[4] Additionally, there is a long history for the use of Pd/C under high pressures of $H_2$ for the reduction of a variety of functional groups (alkenes, nitro, nitriles, imines, aromatics, etc.).[6] Complementary practical applications for the oxidations of diverse classes of functional groups with heterogeneous catalysts remains a relatively underexplored area of interest. Oxidation of alcohols to the corresponding carboxylic acids proves to be challenging in terms of catalyst accessibility and substrate scope, often limited to primarily limited to benzylic alcohols.[7] Use of environmentally benign stoichiometric terminal oxidants, such as molecular oxygen, has led to the employment of a variety of transition metal nanoparticles, largely gold and platinum. Griffin et al. reported a well-defined heterogeneous Pt-based catalyst, performed under air, able to oxidize unactivated primary alcohol to the corresponding carboxylic acids.[8]

Historically, the applications of heterogeneous Platinum Group Metal (PGM) catalysts for oxidation have been restricted predominantly within the domain of sugar chemistry.[9] Catalysts often require the incorporation of various main group promoters; principally bismuth, tellurium, selenium, lead, etc., to assist in the overall substrate oxidation.[10] The addition of additive has been reported to accelerate the reaction rates 20-26 times faster than untreated catalyst.[11] The nature and role of the promoters remains an active avenue of research. Several hypotheses explanations are offered within the literature for the interactions between the PGM catalyst the additive absorbed on the surface or forming an alloy.[12] Some of the most common hypotheses for the role of the promoters are (i) geometric/site blocking (addition of the promoter to a face of the catalyst to prevent side reactions);[13] (ii) promotion of oxygen transfer (where the promoter is oxidized more rapidly than the PGM);[14] (iii) complex formation between reactants and promoter to increase activity;[15] and (iv) bifunctional catalysis (where oxygen or hydroxyl absorbed on the promoter oxidizes the alcohol).[16] Besson highlights the use of a Bi promoted Pd/C catalyst for the oxidation of D-glucose, thought to interact through the oxygen transfer mechanism, in which the Bi interacts with molecular oxygen in situ preventing the formation of catalytically inert $PdO_x$.[17]

Of relevance to the advancement of green chemistry is the oxidation of 5-(hydroxymethyl)furfural (HMF), a biomass-derived compound, to 2,5-furandicarboxylic acid (FDCA). HMF is obtained from three successive acid-catalyzed dehydrogenations of fructose.[18] In addition, FDCA has been proposed as a starting material for various building-block molecules to replace poly(ethylene terephthalate) (bio-renewable alternative to petroleum derived terephthalic acid), succinic acid, 2,5-bis(aminomethyl)-tetrahydrofuran, and various other substituted furans.[19] The desired oxidation can be achieved with the homogeneous Amoco Mid-Century (AMC) catalyst (Co acetate/Mn acetate/Br) in 60% yield.[20] Various heterogeneous catalysts have also been developed for this transformation. Parti et al. reported the use of an Au nanoparticles modified with Pd supported on activated carbon and was able to afford FDCA in 99% yield in 4 hours.[21] Similarly, Hutchings et al. reported the use of a Au nanoparticle catalyst, modified with Cu and supported on titanium oxide, to react the desired di-acid with 99% yield.[22] One of the major drawbacks of the use of gold nanoparticles is the well-documented phenomenon of sintering, leading to catalyst deactivation.[23] A more concentrated reaction, performed with a Pt catalyst modified with Bi supported on carbon, reported by Besson, was able to afford quantitative yield of the di-acid.[24] The use of this PtBi/C catalyst proved to be stable and reusable for the oxidation of HMF.

The need for economical, oxidative transformations remains an unresolved challenge within organic synthesis. As a result, application of an easily prepared supported catalyst for the aerobic oxidation of benzylic and aliphatic alcohols to the corresponding carboxylic acids addresses these challenges. Addition of both Bi and Te promoters enhances both the activity and selectivity of the catalyst. To date, the substrate scope and functional group tolerance displayed are the widest reported for oxidation to carboxylic acids with a heterogeneous catalyst.

Methods and Results

Catalyst development was done in a manner previously reported by our group.[25] Initial screening of Pd on various supports indicated that carbon based supports (i.e. charcoal, activated carbon, etc.) were the most active for the oxidation of 1-octanol. Screening of various solvents indicated that a mixture of water and methanol led to higher activity. Further screening of possible additive effects indicated that a variety of bismuth, tellurium, and selenium sources proved to be the most effective. A more challenging oxidation of cyclohexylmethanol, a relatively sterically constrained alcohol, was used to determine the optimal catalyst. The addition of both bismuth nitrate pentahydrate ($Bi(NO_3)_3 \cdot 5H_2O$) and bismuth telluride ($Bi_2Te_3$) increased the oxidation of cyclohexylmethanol (Table 5). The impact of $Bi_2Te_3$ suggests an optimal tri-metallic catalyst with Pd, Te, and Bi. The addition of metals and metal salts in the presence of Pd/C was $Bi(NO_3)_3 \cdot 5H_2O$ indicated that the combination of Te, $Bi(NO_3)_3 \cdot 5H_2O$, and Pd/C were the optimal catalyst. Interestingly, the composition of the catalyst and the reaction conditions were nearly identical to conditions previously reported from our group for the methyl esterification of alcohols (Example 1).

TABLE 5

Further Screening of Additives for 1-Octanol Oxidation to Carboxylic Acid.

1 mol % Pd Catalyst
5 mol % Additives
1 eq of KOH
$MeOH:H_2O$ (1:9 vol:vol)
1 atm $O_2$, 50° C., 16 h

| Entry | Catalyst | Additives | Yield (Conv.)[a] |
|---|---|---|---|
| 1 | Pd/Char (5 wt. %) | None | 62 (65) |
| 2 | | $Bi_2O_3$ | 73 (99) |
| 3 | | $BiCl_3$ | 63 (64) |
| 4 | | $Bi(NO_3)_3 \cdot 5H_2O$ | 98 (98) |
| 5 | | $Bi_2Te_3$ | 90 (100) |
| 6 | | $Bi(OAc)_3$ | 0 (9) |
| 7 | | $Bi_5O(OH)_9(NO_3)_4$ | 0 (4) |
| 8 | | $Bi(PO_4)$ | 0 (7) |
| 9 | | Bi | 81 (100) |
| 10 | | $TeO_2$ | 59 (63) |
| 11 | | $SeO_2$ | 81 (83) |
| 12 | Pd/Act C (5 wt. %) | None | 55 (58) |
| 13 | | $Bi_2O_3$ | 0 (11) |
| 14 | | $Bi(NO_3)_3 \cdot 5H_2O$ | 0 (9) |
| 15 | | $Bi_2Te_3$ | 0 (12) |
| 16 | | $Bi_2S_3$ | 74 (88) |
| 17 | | Bi | 0 (0) |
| 18 | | $TeO_2$ | 81 (82) |
| 19 | | $SeO_2$ | 93 (95) |

[a]Reactions performed on 1 mmol scale; [$RCH_2OH$] = 1M. $^1H$ NMR yields with trimethyl(phenyl)silane (PhTMS) as internal standard.

An independent effort has been underway to develop the admixture catalyst into a well-defined heterogeneous catalyst.[26] The similarities of the composition of matter for the two admixture catalysts allow the hypothesis to be made that the well-defined catalyst developed for methyl esterification chemistry might also prove to be effective carboxylic acid synthesis.

A comparison of three optimized catalyst systems (1 mol %) Pd/Char (5 wt. % Pd), (5 mol %) $Bi(NO_3)_3 \cdot 5H_2O$, (2.5 mol %) Te;[25] (1 mol %) $PdBi_{0.35}Te_{0.23}/C$ (PBT) (5 wt. %

Pd);[26] and 5 wt. % Pt-1.5 wt. % Bi/C (PtBi/C) for the oxidation to carboxylic acids was performed (Table 6). Oxidation of benzyl alcohol is possible with PBT catalyst to achieve quantitative yields within 4h (Table 6, entry 1). The admixture catalyst system of Pd/Char, Bi(NO$_3$)$_3$.5H$_2$O, and Te was able to achieve moderately high yield (79%) and PtBi/C is able to achieve the oxidation with 89% yield. The oxidation of electron-deficient benzyl alcohol using the add-mixture catalyst achieves a moderate yield (52%) similar to industrial PtBi/C catalyst (57%); however, the yield achieved with PBT is slightly higher (69%) (Table 6, entry 2). In contrast, an electron-rich benzyl alcohol achieves a near quantitative yield with both the admixture (93%) and the well-defined PBT catalyst (97%); however, proves to be challenging for PtBi/C catalyst (53%) (Table 6, entry 3). Aliphatic alcohols are often pitfalls of Pt based catalyst. Oxidation of 1-octanol was challenging for both the admix (11%) and the PtBi/C (25%); however, the well-defined Pd catalyst shows greater ability to oxidize 1-octanol (45%) (Table 6, entry 4). To probe the difference between the three catalyst systems, the oxidation of sterically bulky cyclohexylmethanol was tested (Table 6, entry 5). The admixture catalyst system was inefficient at oxidation of cyclohexylmethanol after 12 h (45%), yet both PBT (100%) and PtBi/C (89%) proved to be able to oxidize cyclohexylmethanol.

alcohol with the Pd/Char catalyst (FIG. 21A), nearly all of the substrate was consumed within the first hour; however, a significant buildup of the aldehyde intermediate (81%) was observed. The aldehyde gradually converted to carboxylic acid and was completely consumed within 8 h. At the same time as the aldehyde disappeared, the carboxylic acid grew in. After 8 h, quantitative yield of the carboxylic acid was achieved and it was stable under reaction conditions. When the oxidation was run with PBT catalyst, full conversion of substrate was seen in 3 h (FIG. 21B). A small buildup of aldehyde (29%) was seen after 1 h, which disappears completely after 2 h. The carboxylic acid was formed in quantitative yield after 3 h.

The oxidation of 1-octanol demonstrated poor yield and conversion when run with Pd/C (FIG. 21C). After 2 h a 41% yield of the carboxylic acid was observed, which gradually increased to a maximum of 62% after 16 h. Unlike the substituted benzyl alcohol, no aldehyde intermediate was observed in the course of the reaction. The reaction run with PBT exhibited a faster reaction rate in addition to higher conversion and yield (FIG. 21D). A quantitative yield was observed after 8 h with excellent mass balance. As noted before, no aldehyde intermediate was observed. The time courses in FIGS. 21A-D showcase the slower rates of aliphatic alcohols when compared to benzylic alcohols. The time courses further indicate that treatment of the supported catalyst with Bi and Te, forming PBT, enhances the activity of the catalyst.

TABLE 2

A comparison between admixture method (5 wt. % Pd/Char, Bi(NO$_3$)$_3$•5H$_2$O, and Te), optimum PdBi$_{0.35}$Te$_{0.23}$/C (PBT) catalyst, and literature reported 5 wt. % Pt-1.5 wt. % Bi/C (PtBi/C).

R–CH$_2$OH (1 mmol, 1M) → [catalyst, 3 eq KOH, O$_2$ (1 atm), MeOH:H$_2$O (1:9 vol:vol), 50° C., X h] → R–COOH

| Entry | Substrate | Catalyst | 0.5 mol % Catalyst | 1.0 mol % Catalyst |
|---|---|---|---|---|
| 1 | benzyl alcohol | Pd/Char, Bi(NO$_3$)$_3$, Te<br>PBT<br>PtBi/C | 79%, 4 h<br>100%, 4 h<br>89%, 4 h | 100%, 4 h |
| 2 | 4-(trifluoromethyl)benzyl alcohol | Pd/Char, Bi(NO$_3$)$_3$, Te<br>PBT<br>PtBi/C | 52%, 4 h<br>69%, 4 h<br>57%, 4 h | 100%, 4 h |
| 3 | 4-methoxybenzyl alcohol | Pd/Char, Bi(NO$_3$)$_3$, Te<br>PBT<br>PtBi/C | 93%, 4 h<br>97%, 4 h<br>53%, 4 h | 100%, 4 h |
| 4 | 1-octanol | Pd/Char, Bi(NO$_3$)$_3$, Te<br>PBT<br>PtBi/C | 11%, 8 h<br>45%, 8 h<br>25%, 8 h | 100%, 8 h |
| 5 | cyclohexylmethanol | Pd/Char, Bi(NO$_3$)$_3$, Te<br>PBT<br>PtBi/C | 45%, 12 h<br>100%, 12 h<br>89%, 12 h | 100%, 12 h |

Figure 22:
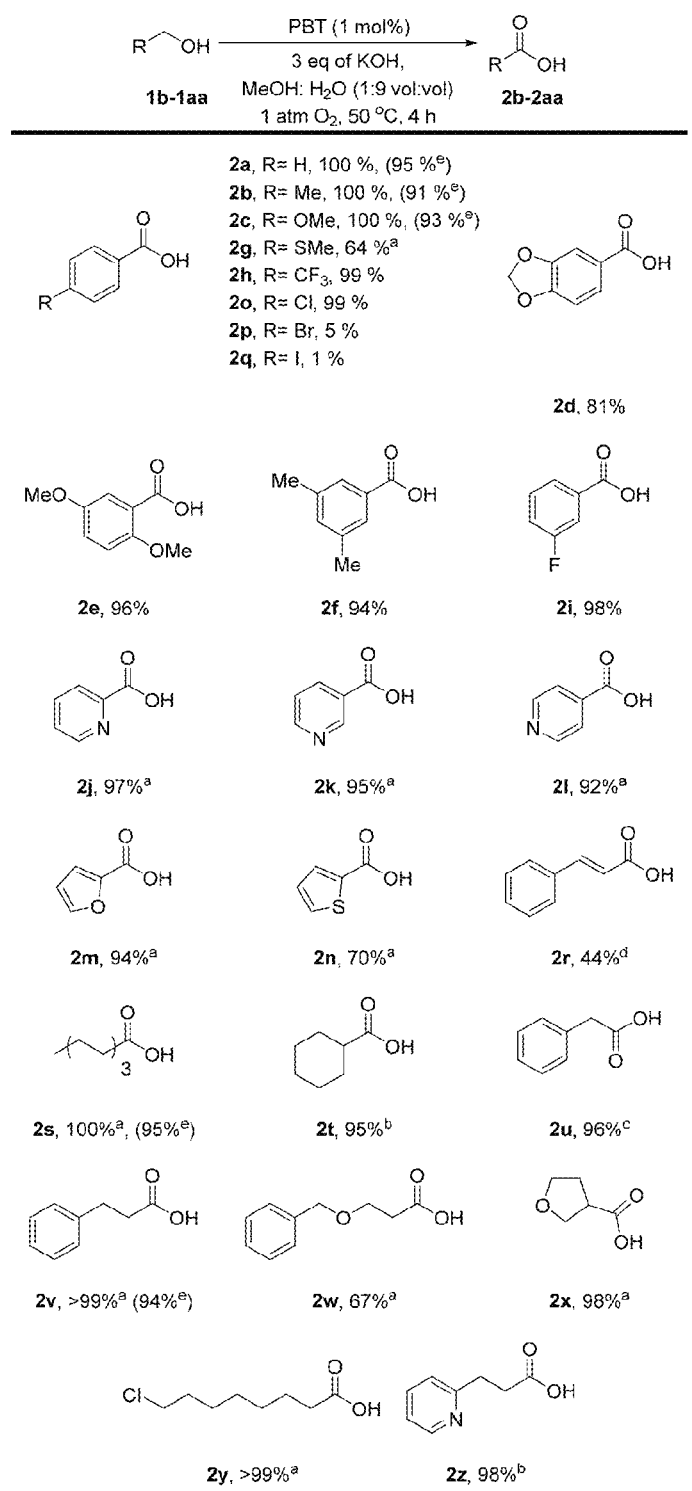
FIG. 22 is a chemical structure schematic demonstrating substrate scope for aerobic alcohol oxidation with PBT catalyst system. Reactions were carried out on 1 mmol scale; [alcohol]=1 M; 1 M, $^1$H NMR yields compared to trimethyl (phenyl)silane as internal standard. $^a$8 h. $^b$12 h. $^c$16 h. $^d$8 h, 25° C. $^e$Isolated yield.

The importance of Bi and Te are apparent in the reaction time courses for model benzylic and aliphatic alcohol substrates (FIG. 21A-D). In the oxidation of 4-methoxybenzyl The substrate scope of PBT displays the widest functional group compatibility reported to date for the oxidation to carboxylic acids with the use of a heterogeneous catalyst (FIG. 22). A wide spectrum of benzyl alcohol substrates (1a-1q), including heterocyclic benzylic alcohols (1j-1n), were subjected to the reaction conditions. In a majority of the cases, a high yield for the carboxylic acids was achieved; tolerant functional groups include ether (2d-2f), thioether (2g). Benzyl alcohols that are electron-poor (2h-2i) cleanly oxidize with excellent yields (>98%).

Halogenated benzyl alcohols substituted in the para position (1o-1q) proved to be susceptible to dehalogenation, particularly in the case of brominated and iododinated substrates (1p and 1q). The chlorine-substituted substrate 1o was able to achieve nearly quantitative yield when subjected to reaction conditions for a short period; however, longer reaction times appeared to facilitate dehalogenation. Of particular interest was the ability of the catalyst to tolerate pyridine motifs, a pitfall for many homogeneous palladium catalysts, and achieve yields greater than 95% (2j-2l). The oxidation of allylic alcohol moiety (1r) achieves rather moderate yield (44%). The low yield can be attributed to a side reaction, alkene hydrogenation, as evident by $^1$H NMR analysis of the reaction mixture.

The functional group tolerance with respect to aliphatic alcohols, similar to benzyl alcohol, is displayed within the substrate table (1s-1z). Simple, straight-chain hydrocarbons proved to be facile substrates (1s). Increasing the steric environment adjacent to the alcohol did not hinder the oxidation (1t). The readily cleaved benzylic C—O bond present in benzylether substrate 1w is tolerated. Tetrahydrofuran structure (1x) was well-tolerated and provided the corresponding acid with excellent yield (98%). A primary alkyl chloride 1y also provided the acid in high yield (>99%). Unlike the aryl chloride 1o, dehalogenation was not observed even at prolonged reaction times. Pyridine moieties are known to chelate to homogenous Pd catalysts[ii]; however, substrate 1j, with an ortho pyridyl group, afforded the carboxylic acid in high yield (97%).

The long-term stability of the catalyst was further demonstrated with a packed-bed reactor. Initial screening of various weight hourly space velocities (WHSV)[iii] for the flow of benzyl alcohol found an optimum of WHSV=620 h$^{-1}$. Under these optimized conditions, a >50h continuous run was done in which the catalyst maintained activity for >60,000 turnovers producing 158 g of benzoic acid.[29] Analysis of the catalyst after by ICP-OES determined loss of approximately 51% of initial mass of Pd, 44% of initial mass of Bi, and 84% of initial mass of Te. Interestingly, while the leeching of metal from the catalyst is significant, the catalyst maintained activity.

Figure 23:
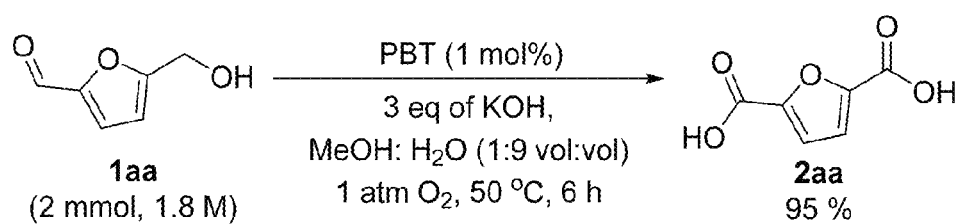
FIG. 23 is a schematic diagram showing the oxidation of HMF to FDCA with PBT catalyst under reaction conditions. HPLC yields with benzoic acid as internal standard. Conditions: 2 mmol scale, [alcohol]=1.8 M, 1 mol % catalyst, 3 eq of KOH, Methanol: Water (1:9 vol: vol), 1 atm 02, 50° C., 6 h.

The PBT catalyst was able to catalyze the oxidation of HMF (1aa) to FDCA (2aa) (FIG. 23). The desired oxidation was achieved with little difficulty; however, there was a strong dependence on the gas-liquid mixing (Table 7). Optimized conditions afford the desired product in 95% yield. Compared to literature precedents, the substrate loading is approximately 2.25 times more concentrated than the next most concentrated example.[24] A comparison to the typical concentration of substrate reveals the loading is approximately 18 times more concentrated, important for HMF chemistry due to the transient stability of both the starting material, HMF, and the product, FDCA, under various reaction conditions.[20,21,22,23]

TABLE 7

Screen of Scale 5-(Hydroxymethyl)furfural (HMF) Oxidation.

1 mol % PBT
3 eq KOH
MeOH:H$_2$O (1:9 vol:vol)
1 atm O$_2$, 50° C., 6 h

| Entry | Scale (mmol) | Yield (Conv.)[a] |
|---|---|---|
| 1[b] | 0.03 | 62 (99) |
| 2[b] | 0.06 | 67 (99) |
| 3[b] | 0.13 | 65 (100) |
| 4[b] | 0.25 | 40 (100) |
| 5[b] | 0.5 | 35 (12) |
| 6[b] | 1 | 38 (100) |
| 7[c] | 2 | 95 (100) |
| 8[c] | 4 | 66 (100) |

[a]Reactions performed on scale indicated; [RCH$_2$OH] = 1M. Yields determined by HPLC with benzoic acid as internal standard.
[b]Disposable 13 mm x 100 mm thick-walled culture tube.
[c]40 mm x 100 mm thick-walled reaction vessel.

To benchmark the ability of the PBT catalyst for the aerobic oxidation of HMF to FDCA a time course comparison of PBT to industrial PtBi catalyst was performed (FIGS. 24A-24B). The initial conversion for both catalysts can be seen as rapidly increasing to full conversion within 1 h. A similar trend has also been reported for the oxidation of HMF in basic media with platinum group metals.[24] The initial high conversion and low yield for FDCA can be attributed to the formation of various intermediates en route to FDCA. The initial rate of PtBi, achieving a maximum yield within 5 hours, of HMF to FDCA appears to be faster than PBT, achieving maximum yield within 6 hours (FIGS. 24A and 24B). FDCA proves to be unstable under the reaction conditions in the presence of PtBi catalyst, and there is a significant loss of product after 8 h (FIG. 24A). A similar trend is seen in the presence of PBT; however, after 8 hours the yield of product is 88%. A loss of 7% yield from the maximum yield after an hour is observed, compared to the loss of approximately 20% yield from the maximum yield after an hour.

In summary, a PBT catalyst previously reported for esterification chemistry proves to be effective for the oxidation of alcohols to carboxylic acids. The catalytic system employs O$_2$ as an environmentally benign oxidant and operates in a water:methanol solvent. The catalyst proves to be a highly effective system for the oxidation of a variety of diverse substrates. Additionally, successful substrates such as aliphatic, allylic, and benzylic alcohols, encompass a much wider substrate scope then previous reported to date. The wide functional group tolerance observed provides unique advantages over other heterogeneous systems, while the recyclability offers distinct advantages over homogenous catalysts, which may employ higher catalyst loadings and/or expensive ligands. Finally, the catalyst is shown to have the ability to oxidize HMF, a biomass derived molecule, to FDCA, a molecule shown to have the ability to potentially replace terephthalic acid. Access to biomass derived feedstock chemicals, such as FDCA, in a viable manner, relative to feedstock derived from petrochemicals, is crucial to commence a paradigm shift in manufacturing to greener practices, and PBT catalyst proves to be a step in that direction.

Abbreviations

PBT, PdBi$_{0.35}$Te$_{0.23}$/C; PtBi/C, 5 wt. % Pt-1.5 wt. % Bi/C; WHSV, Weight Hourly Space Velocities; HMF, 5-(hydroxymethyl)furfural; FDCA, 2,5-furandicarboxylic acid; PET, poly(ethylene terephthalate).

Example 2 References Cited (1) (a) Mallat, T.; Baiker, A. *Chem. Rev.* 2004 104, 3037. (b) Sheldon, R. *Catal. Today* 2000, 57, 157. (c) Sheldon, R. *Catal. Today* 1994, 19, 215.
(2) Zhao, M. Z.; Li, J.; Mano, E.; Song, Z. G.; Tschaen, D. M.; Grabowski, E. J. J.; Reider, P. J. *J. Org. Chem.* 1999, 64, 2564.
(3) Ciufolini, M. A.; Swaminathan, S. *Tetrahedron Lett.* 1989, 30, 3027.
(4) Bowden, K.; Heilbron, I.; Jones, E.; Weedon, B. *J. Chem. Soc.* 1946, 13, 39.
(5) Tungen, J. E.; Aursnes, M.; Hansen, T. V. *Tetrahedron* 2014, 70, 3793.
(6) Pande, P. P. *Asian J. Chem.* 2010, 22, 2549.
(7) An, G.; Ahn, H.; De Castro, K. A.; Rhee, H. *Synthesis-Stuttgart* 2010, 477.
(8) Anderson, R.; Griffin, K.; Johnston, P.; Alsters, P. L. *Adv. Synth. Catal.* 2003, 345, 517.
(9) (a) Prati, L.; Rossi, M. *J. Catal.* 1998, 176, 552. (b) Rossi, M. *J. Catal.* 2002, 2006, 242. (c) Wenkin, M.; Ruiz, P.; Delmon, B.; Devillers, M. *J. Mol. Catal. A: Chem.* 2002, 180, 141.
(10) (a) Fan, A.; Jaenicke, S.; Chuah, G. K. *Org. Biomol. Chem.* 2011, 9, 7720. (b) Bian, R. B.; Shen, J. *Mater. Trans., JIM* 2007, 48, 2252. (c) Alardin, F.; Delmon, B.; Ruiz, P.; Devillers, M. *Catal. Today* 2000, 61, 255.
(11) (a) Mallat, T.; Bodnar, Z.; Hug, P.; Baiker, A. *J. Catal.* 1995, 153, 131. (b) T. Mallat, Z. Bodnar, A. Baiker, Heterogeneous Catalysis and Fine Chemicals III: Studies in Surface Science and Catalysis, *Elsevier*, Amsterdam, 1993, 78, 377.
(12) Witońska, I.; Frajtak, M.; Karski, S. *Appl. Catal., A* 2011, 401, 73.
(13) Kimura, H.; Kimura, A.; Kokubo, I.; Wakisaka, T.; Mitsuda, Y. *Appl. Catal., A* 1993, 95, 143.
(14) Keresszegi, C.; Mallat, T.; Grunwaldt, J. D.; Baiker, A. *J. Catal.* 2004, 225, 138.
(15) Smits, P. C. C.; Kuster, B. F. M.; van der Wiele, K.; van der Baan, S. *Appl. Catal.* 1987, 33, 83.
(16) Mallat, T.; Bodnar, Z.; Baiker, A.; Greis, O.; Strubig, H.; Reller, A. *J. Catal.* 1993, 142, 237.
(17) Besson, M.; Lahmer, F.; Gallezot, P.; Fuertes, P.; Fleche, G. *J. Catal.* 1995, 152, 116.
(18) (a) Daorattanachai, P.; Khemthong, P.; Viriya-empikul, N.; Laosiripojana, N.; Faungnawakij, K. *Carbohydr. Res.* 2012, 363, 58. (b) Daorattanachai, P.; Namuangruk, S.; Viriya-empikul, N.; Laosiripojana, N.; Faungnawakij, K. *J. Ind. Eng. Chem.* 2012, 18, 1893.
(19) Gandini, A.; Silvestre, A. J. D.; Neto, C. P.; Sousa, A. F.; Gomes, M. *J. Polym. Sci., Part A: Polym. Chem.* 2009, 47, 295.
(20) (a) Partenheimer, W.; Grushin, V. V. *Adv. Synth. Catal.* 2001, 343, 102. (b) Sanborn, A., Oxidation of Furfural Compounds. U.S. Pat. No. 8,558,018, Oct. 15, 2013.
(21) Vila, A.; Schiavoni, M.; Campisi, S.; Veith, G. M.; Prati, L. *ChemSusChem* 2013, 6, 609.
(22) Pasini, T.; Piccinini, M.; Blosi, M.; Bonelli, R.; Albonetti, S.; Dimitratos, N.; Lopez-Sanchez, J. A.; Sankar, M.; He, Q.; Kiely, C. J.; Hutchings, G. J.; Cavani, F. *Green Chem.* 2011, 13, 2091.
(23) Ta, N.; Liu, J.; Chenna, S.; Crozier, P.; Li, Y.; Chen, A.; Shen, W. *J. Am. Chem. Soc.* 2012, 134, 20585.
(24) Rass, H. A.; Essayem, N.; Besson, M. *Green Chem.* 2013, 15, 2240.
(25) Powell, A. B.; Stahl, S. S. *Org. Lett.* 2013, 15, 5072.
(26) Mannel, D.; Root, T; Stahl, S. S. *Manuscript in Preparation.*
(27) Lukas, J.; Gunay, A.; Wood, A.; Emmert, M. *Tetrahedron* 2013, 69.

(28) Weight hourly space velocity$(WHSV) = \dfrac{\left(\dfrac{\text{Mass of substrate}}{\text{h}}\right)}{\text{catalyst mass}}$

(29) Turnover Number$(TON) = \dfrac{\text{moles of product}}{\text{moles of catalyst}}$ While a number of embodiments of the present invention have been described above, the present invention is not limited to just these disclosed examples. There are other modifications that are meant to be within the scope of the invention and claims. For example, starting with another organic primary alcohol one could create the corresponding esters and acids. Also, while these methods are especially well suited for the methyl esters, ethyl esters are also formed by analogous reactions using ethanol. Thus, the claims should be looked to in order to judge the full scope of the invention.

We claim:

1. A method for synthesizing an acid from an alcohol, comprising:
    exposing a compound of the formula R—CH$_2$—OH to oxygen gas and methanol-water mixture so as to yield a compound of the formula RCOOH;
    wherein said exposing is in the presence of a catalyst comprising palladium, bismuth and tellurium;
    wherein R is an alkyl, cyclic, amine, or ether, with or without sulfur or halogen content.

2. The method of claim 1, wherein the catalyst further comprises an elemental carbon support in the form of charcoal or activated carbon.

3. The method of claim 1, wherein there is at least 0.1 mol percent palladium, at least 0.01 mol percent bismuth, and at least 0.01 mol percent tellurium in the catalyst.

4. The method of claim 1, in which the bismuth is present in a salt form and the tellurium is present in a metal form.

5. The method of claim 4, wherein the bismuth salt is Bi(NO$_3$)$_3$.5H$_2$O.

6. A method for synthesizing an acid from an alcohol, comprising:

exposing a compound of the formula R—CH$_2$—OH to oxygen gas and water so as to yield a compound of the formula RCOOH;

wherein said exposing is in the presence of a catalyst comprising palladium and a co-catalyst comprising at least two of the following: bismuth, tellurium, lead, cerium, titanium, zinc and niobium;

wherein R is an alkyl, cyclic, amine, ether, or ester, with or without sulfur or halogen content.

* * * * *